(12) United States Patent
Rome et al.

(10) Patent No.: US 8,177,760 B2
(45) Date of Patent: May 15, 2012

(54) VALVED CONNECTOR

(75) Inventors: Guy Rome, West Valley, UT (US); John J. Gunn, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 1966 days.

(21) Appl. No.: 10/844,236

(22) Filed: May 12, 2004

(65) Prior Publication Data

US 2005/0256460 A1   Nov. 17, 2005

(51) Int. Cl.
*A61M 5/00* (2006.01)
*A61M 25/16* (2006.01)
*A61M 25/18* (2006.01)

(52) U.S. Cl. ........................ 604/247; 604/537

(58) Field of Classification Search ............... 604/167.01–167.05, 246, 247, 604/256, 236, 237, 533–538
See application file for complete search history.

(56) References Cited

U.S. PATENT DOCUMENTS

| | | | |
|---|---|---|---|
| 2,263,293 A | 11/1941 | Ewald | |
| 3,288,142 A | 11/1966 | Salomon | |
| 3,593,854 A | 7/1971 | Swank | |
| 3,868,973 A | 3/1975 | Bierman et al. | |
| 3,942,528 A | 3/1976 | Loeser | |
| 3,949,744 A | 4/1976 | Clarke | |
| 3,991,762 A | 11/1976 | Radford | |
| 4,000,739 A | 1/1977 | Stevens | |
| 4,027,668 A | 6/1977 | Dunn | |
| 4,046,144 A | 9/1977 | McFarlane | |
| 4,068,659 A | 1/1978 | Moorehead | |
| 4,068,660 A | 1/1978 | Beck | |
| 4,073,297 A | 2/1978 | Kopp et al. | |
| 4,126,133 A | 11/1978 | Schwartz | |
| 4,128,098 A * | 12/1978 | Bloom et al. ................. | 604/406 |
| 4,159,022 A | 6/1979 | Pevsner | |
| 4,168,699 A | 9/1979 | Hauser | |
| 4,191,186 A | 3/1980 | Keeler | |
| 4,205,675 A | 6/1980 | Vaillancourt | |
| 4,233,982 A | 11/1980 | Bauer et al. | |
| 4,245,635 A | 1/1981 | Kontos | |
| 4,252,131 A | 2/1981 | Hon et al. | |

(Continued)

FOREIGN PATENT DOCUMENTS

WO         03/033049 A2       4/2003

OTHER PUBLICATIONS

U.S. Appl. No. 12/040331, filed Feb. 29, 2008 Final Office Action dated May 26, 2010.

(Continued)

*Primary Examiner* — Matthew F DeSanto
(74) *Attorney, Agent, or Firm* — Rutan & Tucker, LLP

(57) ABSTRACT

A valved connector for controlling the flow of fluid having a valve assembly positioned within a connector housing having a first position wherein the valve assembly prevents fluid flow through the connector housing, and a second position wherein the valve assembly permits fluid flow through the connector housing. The valve assembly may be movable from the first position to the second position by a male luer fitting. The valve assembly is configured for multiple and repeated access and also for minimizing fluid flow restrictions. The valved connector may be designed for use with a catheter to provide for "over the guidewire" placement or replacement techniques with little or no bleed-back or air embolism.

21 Claims, 24 Drawing Sheets

U.S. PATENT DOCUMENTS

| | | | |
|---|---|---|---|
| 4,261,357 A | 4/1981 | Kontos | |
| 4,270,535 A | 6/1981 | Bogue et al. | |
| 4,311,137 A | 1/1982 | Gerard | |
| 4,314,555 A | 2/1982 | Sagae | |
| 4,317,445 A | 3/1982 | Robinson | |
| 4,323,065 A | 4/1982 | Kling | |
| 4,332,254 A | 6/1982 | Lundquist | |
| 4,341,212 A | 7/1982 | Medwid | |
| 4,341,218 A | 7/1982 | U | |
| 4,366,817 A | 1/1983 | Thomas | |
| 4,367,740 A | 1/1983 | Evanoski, III | |
| 4,379,458 A | 4/1983 | Bauer et al. | |
| RE31,272 E | 6/1983 | Pevsner | |
| 4,387,879 A | 6/1983 | Tauschinski | |
| 4,397,647 A | 8/1983 | Gordon | |
| 4,417,886 A | 11/1983 | Frankhouser et al. | |
| 4,424,833 A | 1/1984 | Spector et al. | |
| 4,430,081 A | 2/1984 | Timmermans | |
| 4,436,519 A | 3/1984 | O'Neill | |
| 4,441,495 A | 4/1984 | Hicswa | |
| 4,444,186 A | 4/1984 | Wolvek et al. | |
| 4,464,171 A | 8/1984 | Garwin | |
| 4,465,216 A | 8/1984 | Lauckhardt | |
| 4,473,067 A | 9/1984 | Schiff | |
| 4,479,792 A | 10/1984 | Lazarus et al. | |
| 4,488,545 A | 12/1984 | Shen | |
| 4,508,533 A | 4/1985 | Abramson | |
| 4,512,764 A | 4/1985 | Wunsch | |
| 4,517,979 A | 5/1985 | Pecenka | |
| 4,531,512 A | 7/1985 | Wolvek et al. | |
| 4,531,937 A | 7/1985 | Yates | |
| 4,534,759 A | 8/1985 | Trawoger | |
| 4,540,411 A | 9/1985 | Bodicky | |
| 4,543,092 A | 9/1985 | Mehler et al. | |
| 4,545,367 A | 10/1985 | Tucci | |
| 4,553,968 A | 11/1985 | Komis | |
| 4,559,043 A | 12/1985 | Whitehouse et al. | |
| 4,564,361 A | 1/1986 | Akiyama | |
| 4,565,544 A | 1/1986 | Muller et al. | |
| 4,568,334 A | 2/1986 | Lynn | |
| 4,569,344 A | 2/1986 | Palmer | |
| 4,573,968 A | 3/1986 | Parker | |
| 4,576,142 A | 3/1986 | Schiff | |
| 4,585,439 A | 4/1986 | Michel | |
| 4,585,440 A | 4/1986 | Tchervenkov et al. | |
| 4,610,665 A | 9/1986 | Matsumoto et al. | |
| 4,613,329 A | 9/1986 | Bodicky | |
| 4,619,643 A | 10/1986 | Bai | |
| 4,626,245 A | 12/1986 | Weinstein | |
| 4,629,452 A | 12/1986 | Wahlberg et al. | |
| 4,631,059 A | 12/1986 | Wolvek et al. | |
| 4,632,668 A | 12/1986 | Wilson, Jr. et al. | |
| 4,632,669 A | 12/1986 | Phipps, Sr. et al. | |
| 4,636,197 A | 1/1987 | Chu | |
| 4,638,539 A | 1/1987 | Palmer | |
| 4,642,091 A | 2/1987 | Richmond | |
| 4,644,936 A | 2/1987 | Schiff | |
| 4,650,472 A | 3/1987 | Bates | |
| 4,655,752 A | 4/1987 | Honkanen et al. | |
| 4,673,393 A | 6/1987 | Suzuki et al. | |
| 4,682,980 A | 7/1987 | Suzuki | |
| 4,692,149 A | 9/1987 | Rosenberg et al. | |
| 4,696,296 A | 9/1987 | Palmer | |
| 4,697,573 A | 10/1987 | Schiff | |
| 4,715,857 A | 12/1987 | Juhasz et al. | |
| 4,725,264 A | 2/1988 | Glassman | |
| 4,736,733 A | 4/1988 | Adair | |
| 4,755,173 A | 7/1988 | Konopka et al. | |
| 4,772,266 A | 9/1988 | Groshong | |
| 4,772,267 A | 9/1988 | Brown | |
| 4,782,819 A | 11/1988 | Adair | |
| 4,790,829 A | 12/1988 | Bowden et al. | |
| 4,803,999 A | 2/1989 | Liegner | |
| 4,809,679 A * | 3/1989 | Shimonaka et al. | 600/154 |
| 4,826,480 A | 5/1989 | Diaz et al. | |
| 4,836,199 A | 6/1989 | Palmer | |
| 4,862,874 A | 9/1989 | Kellner | |
| 4,874,373 A | 10/1989 | Luther et al. | |
| 4,878,516 A | 11/1989 | Mathieu | |
| 4,886,508 A | 12/1989 | Washington | |
| 4,888,001 A | 12/1989 | Schoenberg | |
| 4,898,586 A | 2/1990 | McDonough | |
| 4,901,707 A | 2/1990 | Schiff | |
| 4,903,707 A | 2/1990 | Knute et al. | |
| 4,909,793 A | 3/1990 | Vining et al. | |
| 4,915,691 A | 4/1990 | Jones et al. | |
| 4,917,668 A | 4/1990 | Haindl | |
| 4,919,651 A | 4/1990 | Doane | |
| 4,921,479 A | 5/1990 | Grayzel | |
| 4,925,444 A | 5/1990 | Orkin et al. | |
| 4,925,448 A | 5/1990 | Bazaral | |
| 4,929,236 A | 5/1990 | Sampson | |
| 4,930,341 A | 6/1990 | Euteneuer | |
| 4,936,832 A | 6/1990 | Vaillancourt | |
| 4,944,728 A | 7/1990 | Carrell et al. | |
| 4,946,449 A | 8/1990 | Davis, Jr. | |
| 4,950,224 A | 8/1990 | Gorsuch et al. | |
| 4,978,344 A | 12/1990 | Dombrowski et al. | |
| 4,988,062 A | 1/1991 | London | |
| 4,994,041 A | 2/1991 | Dombrowski et al. | |
| 4,998,923 A | 3/1991 | Samson et al. | |
| 5,000,740 A | 3/1991 | Ducharme et al. | |
| 5,000,745 A | 3/1991 | Guest et al. | |
| 5,007,901 A | 4/1991 | Shields | |
| 5,009,391 A * | 4/1991 | Steigerwald | 251/149.1 |
| 5,030,202 A | 7/1991 | Harris | |
| 5,035,686 A | 7/1991 | Crittenden et al. | |
| 5,051,109 A | 9/1991 | Simon | |
| 5,053,013 A | 10/1991 | Ensminger et al. | |
| 5,053,014 A | 10/1991 | Van Heugten | |
| 5,057,093 A | 10/1991 | Clegg et al. | |
| 5,064,416 A * | 11/1991 | Newgard et al. | 604/167.03 |
| 5,084,023 A | 1/1992 | Lemieux | |
| 5,087,251 A | 2/1992 | Heyman et al. | |
| 5,092,857 A | 3/1992 | Fleischhacker | |
| 5,102,394 A | 4/1992 | Lasaitis et al. | |
| 5,108,374 A | 4/1992 | Lemieux | |
| 5,108,380 A | 4/1992 | Herlitze et al. | |
| 5,114,399 A | 5/1992 | Kovalcheck | |
| 5,114,408 A * | 5/1992 | Fleischhaker et al. | 604/167.04 |
| 5,116,323 A | 5/1992 | Kreuzer et al. | |
| 5,127,905 A | 7/1992 | Lemieux | |
| 5,131,407 A | 7/1992 | Ischinger et al. | |
| 5,135,483 A | 8/1992 | Wagner et al. | |
| 5,135,501 A | 8/1992 | Cameron | |
| 5,140,983 A | 8/1992 | Jinotti | |
| 5,146,925 A | 9/1992 | Snow | |
| 5,147,334 A | 9/1992 | Moss | |
| 5,151,105 A | 9/1992 | Kwan-Gett | |
| 5,156,596 A | 10/1992 | Balbierz et al. | |
| 5,158,545 A | 10/1992 | Trudell et al. | |
| 5,158,569 A | 10/1992 | Strickland et al. | |
| 5,163,903 A | 11/1992 | Crittenden et al. | |
| 5,165,420 A | 11/1992 | Strickland | |
| 5,171,222 A | 12/1992 | Euteneuer et al. | |
| 5,176,655 A | 1/1993 | McCormick et al. | |
| 5,178,612 A | 1/1993 | Fenton, Jr. | |
| 5,188,603 A | 2/1993 | Vaillancourt | |
| 5,191,898 A | 3/1993 | Millar | |
| 5,192,273 A | 3/1993 | Bierman | |
| 5,197,952 A | 3/1993 | Marcadis et al. | |
| 5,201,721 A | 4/1993 | Lee et al. | |
| 5,205,830 A | 4/1993 | Dassa et al. | |
| 5,217,435 A | 6/1993 | Kring | |
| 5,233,979 A | 8/1993 | Strickland | |
| 5,234,406 A | 8/1993 | Drasner et al. | |
| 5,234,407 A | 8/1993 | Teirstein et al. | |
| 5,234,437 A | 8/1993 | Sepetka | |
| 5,236,417 A | 8/1993 | Wallis | |
| 5,242,413 A * | 9/1993 | Heiliger | 604/167.04 |
| 5,242,425 A | 9/1993 | White et al. | |
| 5,243,995 A | 9/1993 | Maier | |
| 5,246,012 A | 9/1993 | Strickland | |
| RE3,441 E | 10/1993 | Lemieux | |
| 5,254,104 A | 10/1993 | Furlow et al. | |
| 5,261,877 A | 11/1993 | Fine et al. | |
| 5,261,887 A | 11/1993 | Walker | |

| | | | | | | |
|---|---|---|---|---|---|---|
| 5,261,916 A | 11/1993 | Engelson | | 5,779,688 A | 7/1998 | Imran et al. |
| 5,263,932 A | 11/1993 | Jang | | 5,795,334 A | 8/1998 | Cochrane, III |
| RE34,466 E | 12/1993 | Taylor et al. | | 5,795,340 A | 8/1998 | Lang |
| 5,269,771 A | 12/1993 | Thomas et al. | | 5,795,341 A | 8/1998 | Samson |
| 5,281,200 A | 1/1994 | Corso, Jr. et al. | | 5,797,886 A | 8/1998 | Roth et al. |
| 5,303,714 A | 4/1994 | Abele et al. | | 5,800,399 A | 9/1998 | Bogert et al. |
| 5,304,195 A | 4/1994 | Twyford, Jr. et al. | | 5,807,328 A | 9/1998 | Briscoe |
| 5,312,374 A | 5/1994 | Gurmarnik | | 5,810,869 A | 9/1998 | Kaplan et al. |
| 5,322,518 A | 6/1994 | Schneider et al. | | 5,830,188 A | 11/1998 | Abouleish |
| 5,328,482 A | 7/1994 | Sircom et al. | | 5,830,228 A | 11/1998 | Knapp et al. |
| 5,330,434 A | 7/1994 | McFarlane | | 5,843,046 A | 12/1998 | Motisi et al. |
| 5,330,449 A | 7/1994 | Prichard et al. | | 5,843,091 A | 12/1998 | Holsinger et al. |
| 5,333,607 A | 8/1994 | Kee et al. | | 5,843,113 A | 12/1998 | High |
| 5,338,301 A | 8/1994 | Diaz | | 5,853,391 A | 12/1998 | Bell |
| 5,346,483 A | 9/1994 | Thaxton, Sr. | | 5,853,400 A | 12/1998 | Samson |
| 5,348,541 A | 9/1994 | Lyell | | 5,861,024 A | 1/1999 | Rashidi |
| 5,356,394 A | 10/1994 | Farley et al. | | 5,876,400 A | 3/1999 | Songer |
| 5,358,490 A | 10/1994 | Henry et al. | | 5,882,335 A | 3/1999 | Leone et al. |
| 5,368,563 A | 11/1994 | Lonneman et al. | | 5,891,100 A | 4/1999 | Fleckenstein |
| 5,370,610 A | 12/1994 | Reynolds | | 5,904,665 A | 5/1999 | Muharib |
| 5,372,583 A | 12/1994 | Roberts et al. | | 5,919,164 A | 7/1999 | Andersen |
| 5,382,242 A | 1/1995 | Horton et al. | | 5,919,174 A | 7/1999 | Hanson |
| 5,390,678 A | 2/1995 | Gesswein et al. | | 5,928,200 A | 7/1999 | Thorne et al. |
| 5,397,305 A | 3/1995 | Kawula et al. | | 5,928,208 A | 7/1999 | Chu et al. |
| 5,405,336 A | 4/1995 | Austin et al. | | 5,954,691 A | 9/1999 | Prosl |
| 5,407,431 A | 4/1995 | Botich et al. | | 5,957,898 A * | 9/1999 | Jepson et al. .................. 604/256 |
| 5,413,562 A | 5/1995 | Swauger | | 5,964,734 A | 10/1999 | Peeno |
| 5,417,672 A | 5/1995 | Nita et al. | | 6,013,058 A | 1/2000 | Prosl et al. |
| 5,443,481 A | 8/1995 | Lee | | 6,019,777 A | 2/2000 | Mackenzie |
| 5,449,343 A | 9/1995 | Samson et al. | | 6,024,727 A | 2/2000 | Thorne et al. |
| 5,449,345 A | 9/1995 | Taylor et al. | | 6,027,489 A | 2/2000 | Galato |
| 5,454,798 A | 10/1995 | Kubalak et al. | | 6,033,390 A | 3/2000 | von Dyck |
| 5,458,585 A | 10/1995 | Salmon et al. | | 6,036,171 A | 3/2000 | Weinheimer et al. |
| 5,474,534 A | 12/1995 | Schlitt | | 6,042,577 A | 3/2000 | Chu et al. |
| 5,480,385 A | 1/1996 | Thorne et al. | | 6,056,726 A | 5/2000 | Isaacson |
| 5,487,734 A | 1/1996 | Thorne et al. | | 6,074,362 A | 6/2000 | Jang et al. |
| 5,487,757 A | 1/1996 | Truckai et al. | | 6,089,539 A | 7/2000 | Kouda |
| 5,489,271 A | 2/1996 | Andersen | | 6,089,541 A | 7/2000 | Weinheimer et al. |
| 5,489,274 A | 2/1996 | Chu et al. | | 6,102,884 A | 8/2000 | Squitieri |
| 5,489,275 A | 2/1996 | Thompson et al. | | RE36,857 E | 9/2000 | Euteneuer et al. |
| 5,489,771 A | 2/1996 | Beach et al. | | 6,126,641 A | 10/2000 | Shields |
| 5,520,645 A | 5/1996 | Imran et al. | | 6,156,010 A | 12/2000 | Kuracina et al. |
| 5,520,647 A | 5/1996 | Solar | | 6,156,035 A | 12/2000 | Songer |
| 5,520,654 A | 5/1996 | Wahlberg | | 6,156,053 A | 12/2000 | Gandhi et al. |
| 5,522,883 A | 6/1996 | Slater et al. | | 6,165,156 A | 12/2000 | Cesarczyk et al. |
| 5,535,785 A * | 7/1996 | Werge et al. .................. 137/843 | | 6,183,444 B1 | 2/2001 | Glines et al. |
| 5,540,658 A | 7/1996 | Evans et al. | | 6,190,304 B1 | 2/2001 | Downey et al. |
| 5,542,927 A | 8/1996 | Thorne et al. | | 6,190,360 B1 | 2/2001 | Iancea et al. |
| 5,549,645 A | 8/1996 | Frey | | 6,190,370 B1 | 2/2001 | Tsui |
| 5,549,708 A | 8/1996 | Thorne et al. | | 6,193,691 B1 | 2/2001 | Beardsley |
| 5,554,118 A | 9/1996 | Jang | | 6,206,851 B1 | 3/2001 | Prosl |
| 5,554,141 A | 9/1996 | Wendler | | 6,213,978 B1 | 4/2001 | Voyten |
| 5,562,633 A | 10/1996 | Wozencroft et al. | | 6,213,979 B1 | 4/2001 | Bierman |
| 5,569,186 A | 10/1996 | Lord et al. | | 6,217,569 B1 | 4/2001 | Fiore |
| 5,616,135 A | 4/1997 | Thorne et al. | | 6,234,992 B1 | 5/2001 | Haight et al. |
| 5,620,424 A | 4/1997 | Abramson | | 6,258,066 B1 | 7/2001 | Urich |
| 5,624,413 A | 4/1997 | Markel et al. | | 6,261,316 B1 | 7/2001 | Shaolian et al. |
| 5,643,227 A | 7/1997 | Stevens | | 6,296,627 B1 | 10/2001 | Edwards |
| 5,643,296 A | 7/1997 | Hundertmark et al. | | 6,315,789 B1 | 11/2001 | Cragg |
| 5,645,048 A | 7/1997 | Brodsky et al. | | 6,319,227 B1 | 11/2001 | Mansouri-Ruiz |
| 5,658,264 A | 8/1997 | Samson | | 6,325,777 B1 | 12/2001 | Zadno-Azizi et al. |
| 5,685,860 A | 11/1997 | Chang et al. | | 6,325,785 B1 | 12/2001 | Babkes et al. |
| 5,686,096 A | 11/1997 | Khan et al. | | 6,355,061 B1 | 3/2002 | Quiachon et al. |
| 5,688,253 A | 11/1997 | Paradis | | 6,358,230 B1 | 3/2002 | Davey |
| 5,709,661 A | 1/1998 | Van Egmond et al. | | 6,358,276 B1 | 3/2002 | Edwin |
| 5,713,850 A | 2/1998 | Heilmann et al. | | 6,379,338 B1 | 4/2002 | Garvin |
| 5,713,854 A | 2/1998 | Inderbitzen et al. | | 6,398,755 B1 | 6/2002 | Belef et al. |
| 5,713,876 A | 2/1998 | Bogert et al. | | 6,440,097 B1 | 8/2002 | Kupiecki |
| 5,716,347 A | 2/1998 | Gibbs et al. | | 6,468,248 B1 | 10/2002 | Gibbs |
| 5,738,660 A | 4/1998 | Luther | | 6,475,189 B1 | 11/2002 | Lilley, Jr. |
| 5,738,667 A | 4/1998 | Solar | | 6,482,188 B1 | 11/2002 | Rogers et al. |
| 5,743,883 A | 4/1998 | Visconti | | 6,485,473 B1 | 11/2002 | Lynn |
| 5,749,826 A | 5/1998 | Faulkner | | 6,485,500 B1 | 11/2002 | Kokish et al. |
| 5,749,857 A | 5/1998 | Cuppy | | 6,497,683 B1 | 12/2002 | Pagni |
| 5,749,861 A | 5/1998 | Guala et al. | | 6,508,790 B1 | 1/2003 | Lawrence |
| 5,755,685 A | 5/1998 | Andersen | | 6,551,283 B1 * | 4/2003 | Guo et al. .................. 604/167.06 |
| 5,755,709 A | 5/1998 | Cuppy | | 6,554,805 B2 | 4/2003 | Hiejima et al. |
| 5,772,628 A | 6/1998 | Bacich et al. | | 6,569,180 B1 | 5/2003 | Sirhan et al. |
| 5,779,678 A | 7/1998 | Carter | | 6,572,578 B1 | 6/2003 | Blanchard |

| | | |
|---|---|---|
| 6,575,960 B2 | 6/2003 | Becker et al. |
| 6,579,254 B1 | 6/2003 | McNary et al. |
| 6,579,261 B1 | 6/2003 | Kawamura |
| 6,651,956 B2 | 11/2003 | Miller |
| 6,695,820 B1 | 2/2004 | Armstrong et al. |
| 7,063,685 B2 | 6/2006 | Rome |
| 2002/0099326 A1 | 7/2002 | Wilson et al. |
| 2003/0098430 A1 | 5/2003 | Leinsing et al. |
| 2004/0034324 A1 | 2/2004 | Seese et al. |
| 2004/0034333 A1 | 2/2004 | Seese et al. |
| 2004/0039373 A1 | 2/2004 | Harding et al. |
| 2004/0097903 A1 | 5/2004 | Raulerson |
| 2004/0122416 A1 | 6/2004 | Schweikert et al. |
| 2004/0122418 A1 | 6/2004 | Voorhees |
| 2004/0176739 A1 | 9/2004 | Stephens et al. |
| 2004/0193118 A1 | 9/2004 | Bergeron |
| 2005/0113805 A1 | 5/2005 | Devellian et al. |
| 2005/0192537 A1 | 9/2005 | Osborne et al. |

OTHER PUBLICATIONS

U.S. Appl. No. 12/040331, filed Feb. 29, 2008 Non-Final Office Action dated Nov. 17, 2009.

U.S. Appl. No. 12/040331, filed Feb. 29, 2008 Notice of Allowance dated Mar. 2, 2011.

* cited by examiner

VALVED CONNECTOR

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A COMPACT DISK APPENDIX

Not applicable.

FIELD OF THE INVENTION

The present invention is generally in the field of medical devices. More particularly, the present invention relates to a valved connector for use with a catheter that uses a standard luer fitting to allow multiple and repeated access to the connector and to minimize fluid flow restrictions.

BACKGROUND OF THE INVENTION

There are a variety of conditions that require injection of fluids into, or withdrawing fluids from, parts of a body below the surface of the skin of the body. It is common to use an implanted catheter to repeatedly access the vascular system of a patient. A flexible guidewire placed in the vascular system can be used to facilitate placement of the catheter, but its use can prevent capping the catheter to prevent fluid loss from or air entering the vascular system during placement. After catheter placement, it is common to attach a valved cap to the catheter connector(s) to prevent fluid loss from or air entering the catheter and vascular system.

U.S. Pat. No. 6,575,960 (Bleed Back Control Assembly and Method) relates to a Y-valved connector. The 'Y-connector' includes a sealing valve that is normally closed except when accessed with a small diameter tube or wire. The sealing valve does not completely prevent air or fluid leakage, but relies on a second user compressible valve to provide a complete seal.

In short, there are several problems with the current valves. The flow path through the valve is restricted due to a restricted cross-sectional area. There is a dead space above or below the valve where blood accumulates, which makes it difficult to clean the valve. The current valves are not designed for use with a guidewire traversing through the same valve. Also, the valves cannot be accessed multiple times; they are typically screwed on to the catheter and discarded after use. Therefore, there is a need for a valved connector that solves the above-mentioned problems and thereby reduces the risk of contamination and permits repeated use of the valved connector.

SUMMARY OF THE INVENTION

Accordingly, a valved connector is provided herein, which could be utilized in connection with a catheter to prevent bleed back and air embolism, while overcoming the drawbacks of the prior art.

In one embodiment of the present invention a valved connector for controlling the flow of fluid comprises a connector housing having an inlet and an outlet, said inlet being configured to receive a male luer fitting, and a valve assembly positioned within said connector housing having a first position wherein said valve assembly prevents fluid flow through said connector housing, and a second position wherein said valve assembly permits fluid flow through said connector housing, wherein said valve assembly is movable from said first position to said second position by said male luer fitting, said valve assembly comprising a valve housing, an introducer valve configured to permit passage of an introducer therethrough, said introducer valve comprising a first slit septum, a hole septum and a second slit septum, wherein said hole septum is positioned between said first slit septum and said second slit septum, and a biasing element configured to bias said valve assembly in said first position.

In another embodiment of the present invention a valved connector for controlling the flow of fluid, comprising a connector housing having an inlet and an outlet, said inlet being configured to receive a male luer fitting, and a valve assembly having a first position wherein said valve assembly prevents fluid flow through said connector housing, and a second position wherein said valve assembly permits fluid flow through said connector housing, said valve assembly being biased in said first position and being movable from said first position to said second position by said male luer fitting, said valve assembly comprising a valve element comprising an upper portion, a slit portion and a lower portion, wherein said upper and lower portions have bores extending through said valve element to said slit portion, and a support disk having an hole through the center thereof, wherein said valve element is positioned on said support disk.

In another embodiment of the present invention a valved connector for controlling the flow of fluid, comprising a connector housing having an inlet and an outlet, said inlet being configured to receive a male luer fitting, and a valve assembly positioned within said connector housing having a first position wherein said valve assembly prevents fluid flow through said connector housing, and a second position wherein said valve assembly permits fluid flow through said connector housing, wherein said valve assembly is movable from said first position to said second position by said male luer fitting, said valve assembly comprising a flow-through disk comprising at least one protrusion, a sealing element configured to seal against said head in said first position, and a biasing element in contact with said sealing element and configured to bias said valve assembly in said first position.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

In the accompanying drawings, reference characters refer to the same parts throughout the different views. The drawings are intended for illustrating some of the principles of providing a valved connector and are not intended to limit the description in any way. The drawings are not necessarily to scale, emphasis instead being placed upon illustrating the depicted principles in a clear manner.

DETAILED DESCRIPTION OF THE INVENTION

Figure 1A:
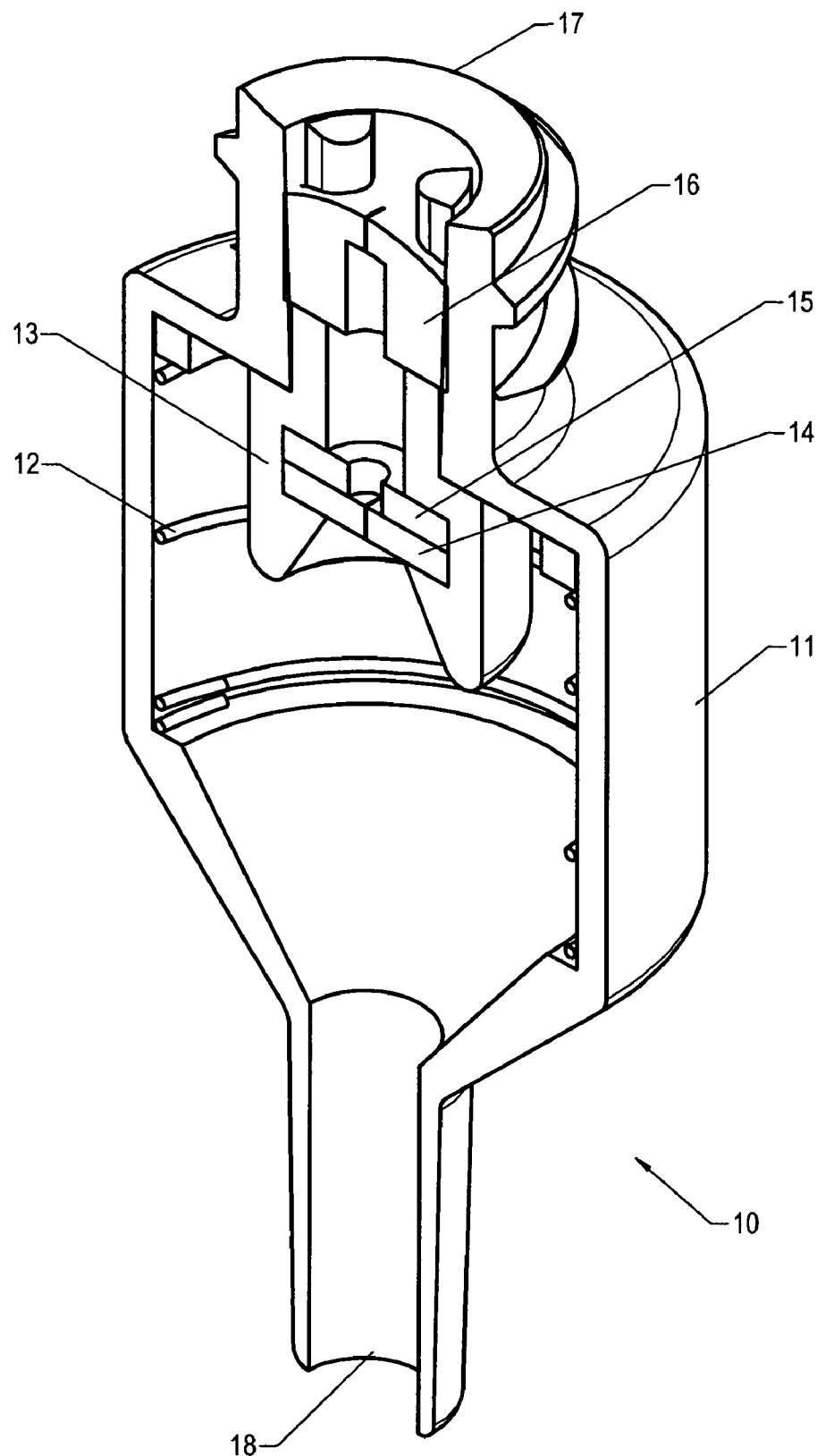
FIGS. 1A-1K illustrate different aspects of a valved connector according to the present invention.

The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The valved connector may be used for facilitating the introduction or removal a fluid to or from a body. The valved connector may be temporarily attached to a luer fitting connector of a catheter or it may be permanently attached to the catheter in lieu of the luer fitting connection. The valved connector could be coupled to a catheter, which may be utilized for chronic excess fluid drainage from a body. In other applications, the valved connector could be coupled to an implantable electromechanically powered and/or magnetically coupled vesicular pump to permit assisted flow of a fluid into or out of a body. This flow may be uni-directional. As used herein, the term "male luer fitting" is defined as a cylindrical device or portion of a device having a blunt end for insertion into the inlet of a connector housing, which term can be used interchangeably with the term "blunt cannula." Examples of materials for the valve housing and selected other components of the valved connector of the present invention are plastic and metal, with the biasing elements being made of materials such as stainless steel and silicone, and the valve component being made of materials such as silicone.

The valved connectors of the present invention are advantageous in many aspects, a few of which are now described. First, in some embodiments, the valved connectors include an introducer valve that is normally closed except when accessed with a small diameter tube or wire, but which includes an additional sealing (donut) valve that completely prevents air or fluid leakage while accessed. Second, prior art "Y-connectors" such as those of U.S. Pat. No. 6,575,960 would allow unrestricted fluid flow but do not incorporate the safety features of the valved connector design of this invention (i.e., normally closed except when accessed). Access of the prior art devices' connection requires clamping of the catheter any time the luer 'Y' fitting is accessed to prevent fluid flow and/or air embolism, which is not required by the valved connector design of the present invention. Third, the valved connector of the present invention provides patient safety by insuring the connector(s) are sealed (valve closed) except when a male luer fitting is inserted through the connector housing inlet (valve open). Fourth, the valved connector may be accessed multiple times without requiring replacement. Fifth, the valved connector is significantly smaller typically 0.5" diameter×1.0" length and can replace the standard luer fitting typically used on catheter connections. It should be appreciated that there are many more advantages enjoyed by the present invention and the foregoing are merely examples of such advantages.

The valved connectors of this invention are broadly classified as Type 1 and Type 2 valved connectors. The Type 1 valved connectors contain an orifice for passage of an introducer such as a guidewire. Some embodiments of the Type 1 valved connectors include: (a) spring-actuated valve assembly; (b) spring-actuated valve assembly having an introducer valve within a cavity of the valve housing; (c) compression ring actuated valve assembly; and (d) flexible valve element on a support disk. The Type 1 design provides for an "over the guidewire" placement or replacement technique with no bleed-back or air embolism. This is due to the triple layer design of a slit opening, followed by a hole opening, followed by another slit opening.

The Type 1 valved connector could be integral with the catheter to avoid problems occurring in prior art devices that necessitate the discarding thereof after use. As is apparent from the drawings, the valved connector has a valve system for fluid flow and for the guide wire. The fluid flow valve is a spring-like biasing mechanism, wherein a valve housing is pressed against by a male luer fitting, which in turn presses against a biasing element to open the valve assembly. The valve assembly is biased in the closed position by the biasing element. From the inlet to the outlet direction, the valve assembly may comprise an upper slit septum followed by a hole septum, followed by a lower slit septum that together form an introducer valve within the valve assembly. In preferred embodiments, a cavity is provided between the upper slit septum and the hole septum, rather than sandwiching the septa or rather than providing space above and below the valve assembly in order to eliminate dead space that leads to various problems. Thus, the advantages of the valved connector of the present invention include the allowance of better fluid flow therethrough, the removal of dead space, guidewire accessibility both proximally and distally, and having the ability to be accessed numerous times without failure or problems generally associated with such valved systems.

The Type 2 valved connectors illustrated herein have no ability to permit passage of an introducer, such as a guidewire. It should be noted, however, that while the Type 2 valved connectors shown herein do not have an orifice for the passage of an introducer, such an orifice could be fashioned to provide for an "over the guidewire" placement or replacement technique with no bleed-back or air embolism. Some embodiments of the Type 2 valved connectors include: (a) a valve having a flow-through disk, a compression ring and a sealing device; and (b) a valve having a flow-through disk on a compression ring.

Figure 1B:
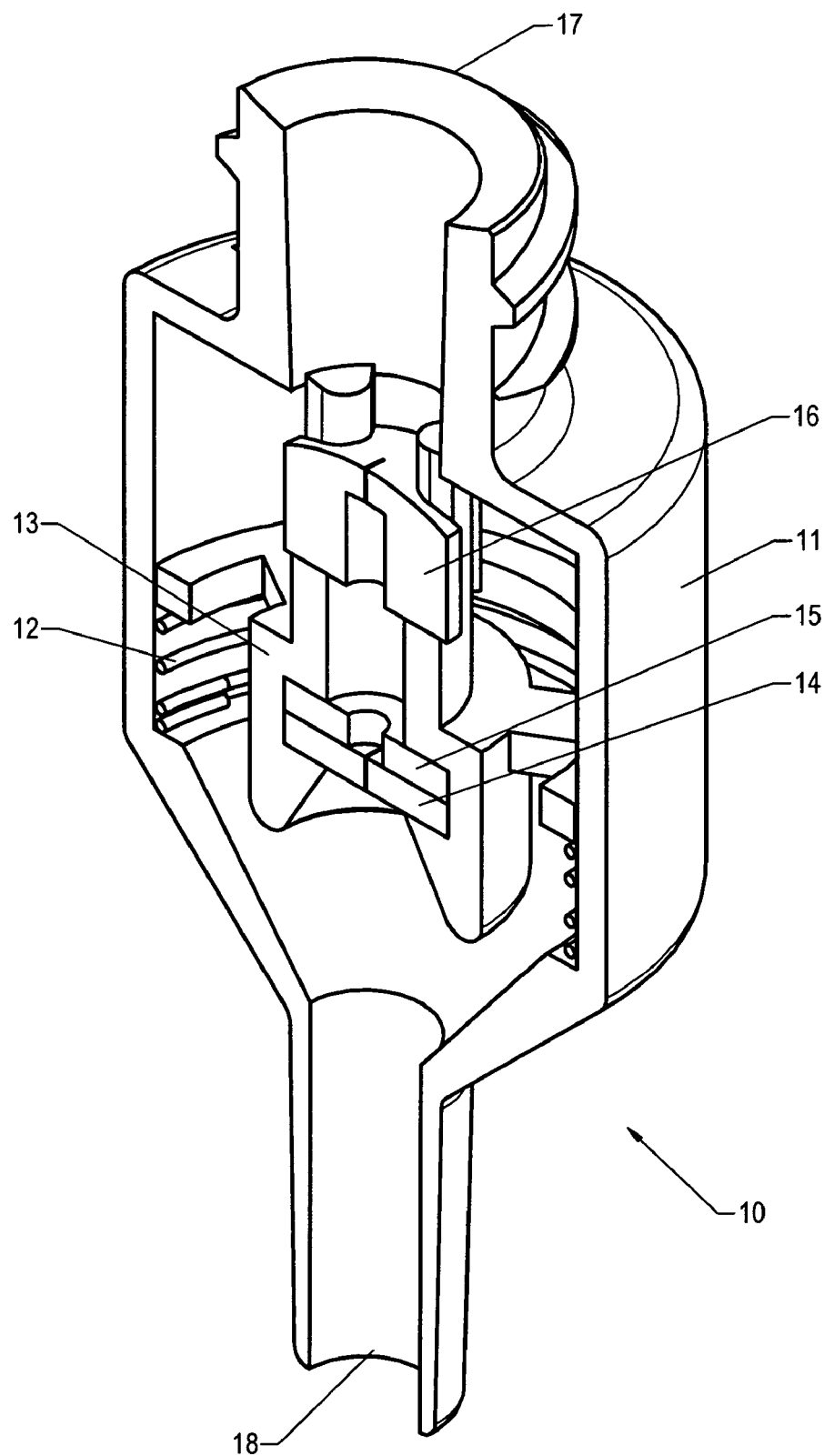
Figure 1C:
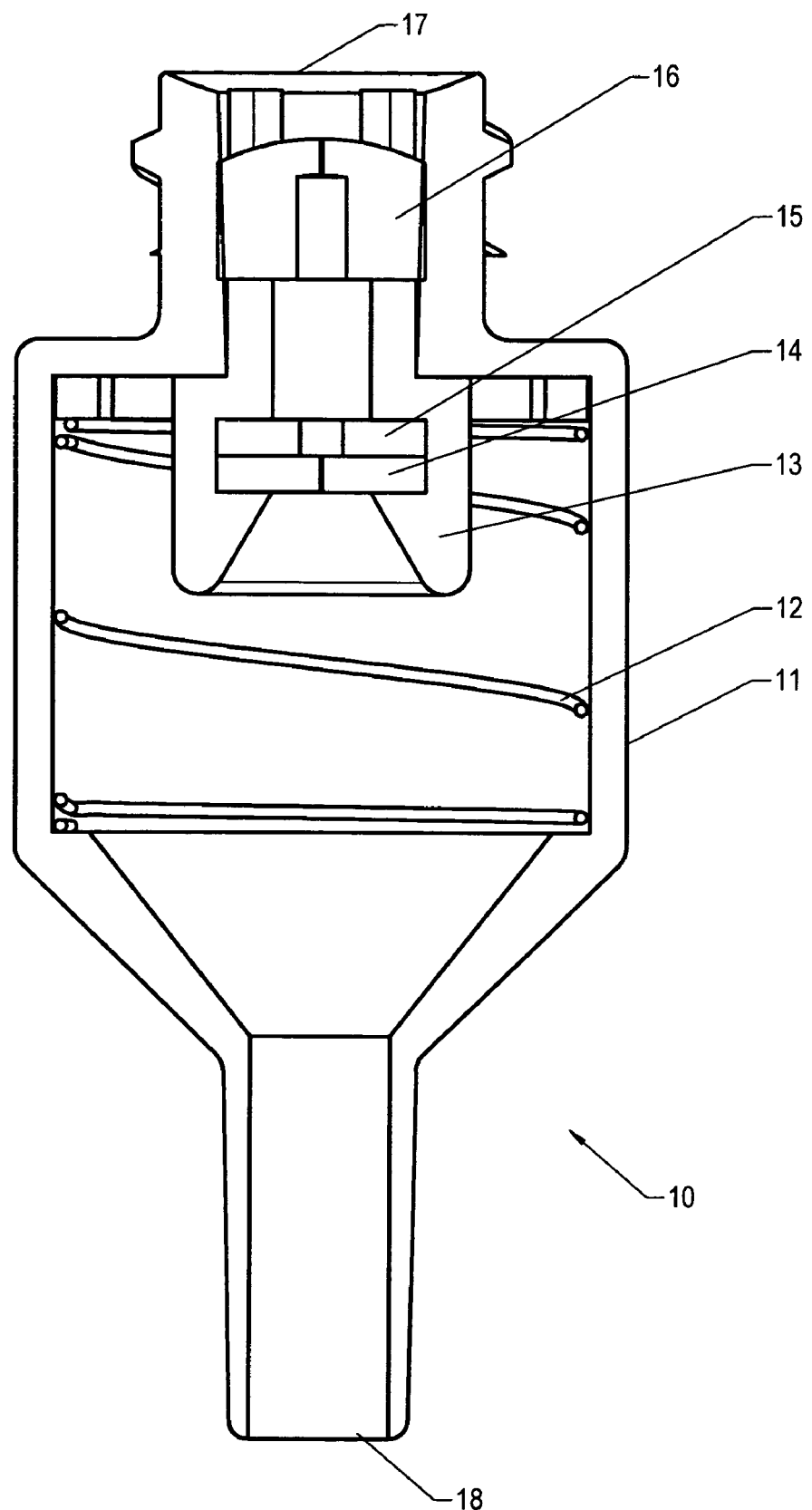
Figure 1D:
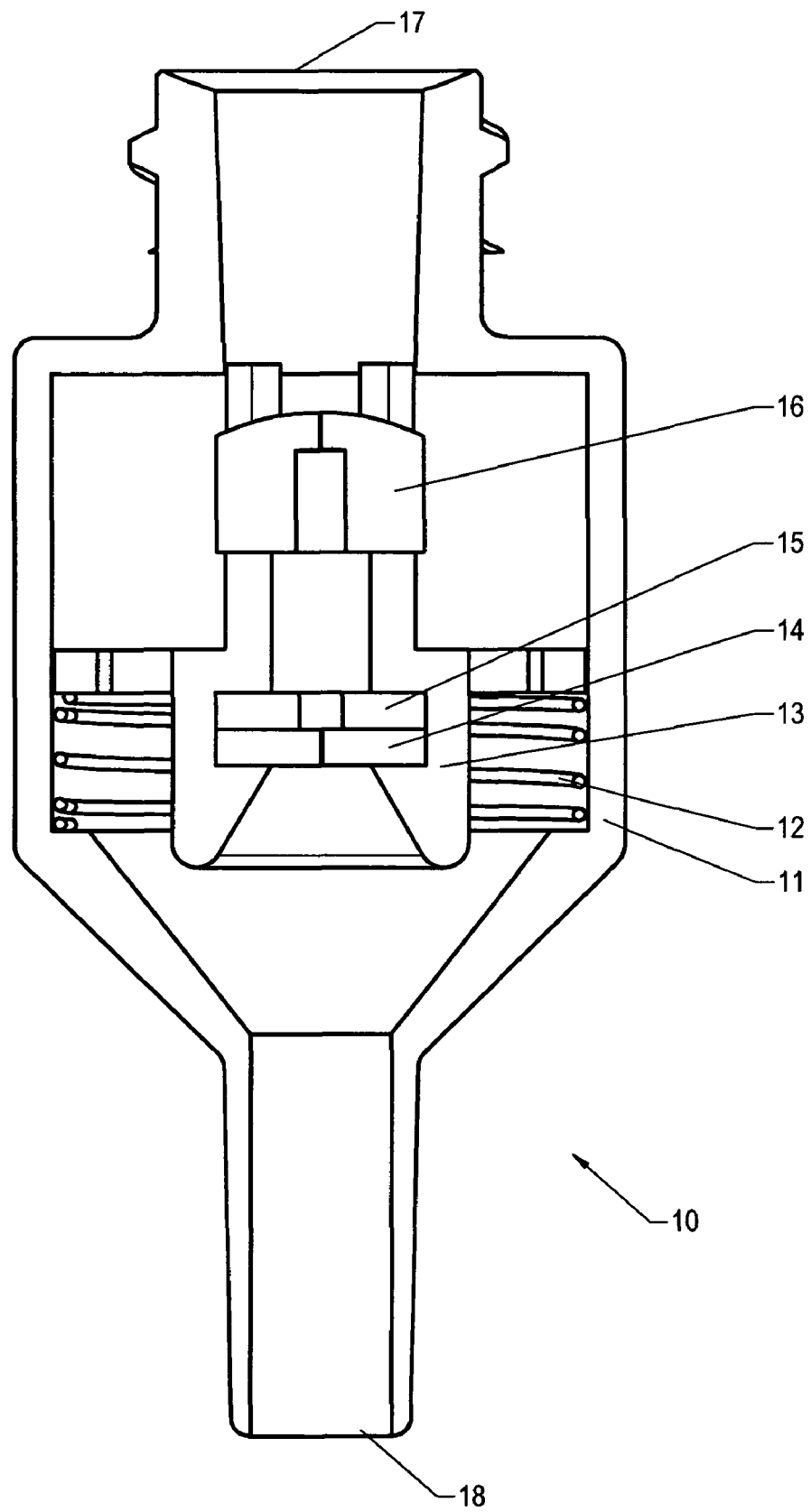
Figure 1E:
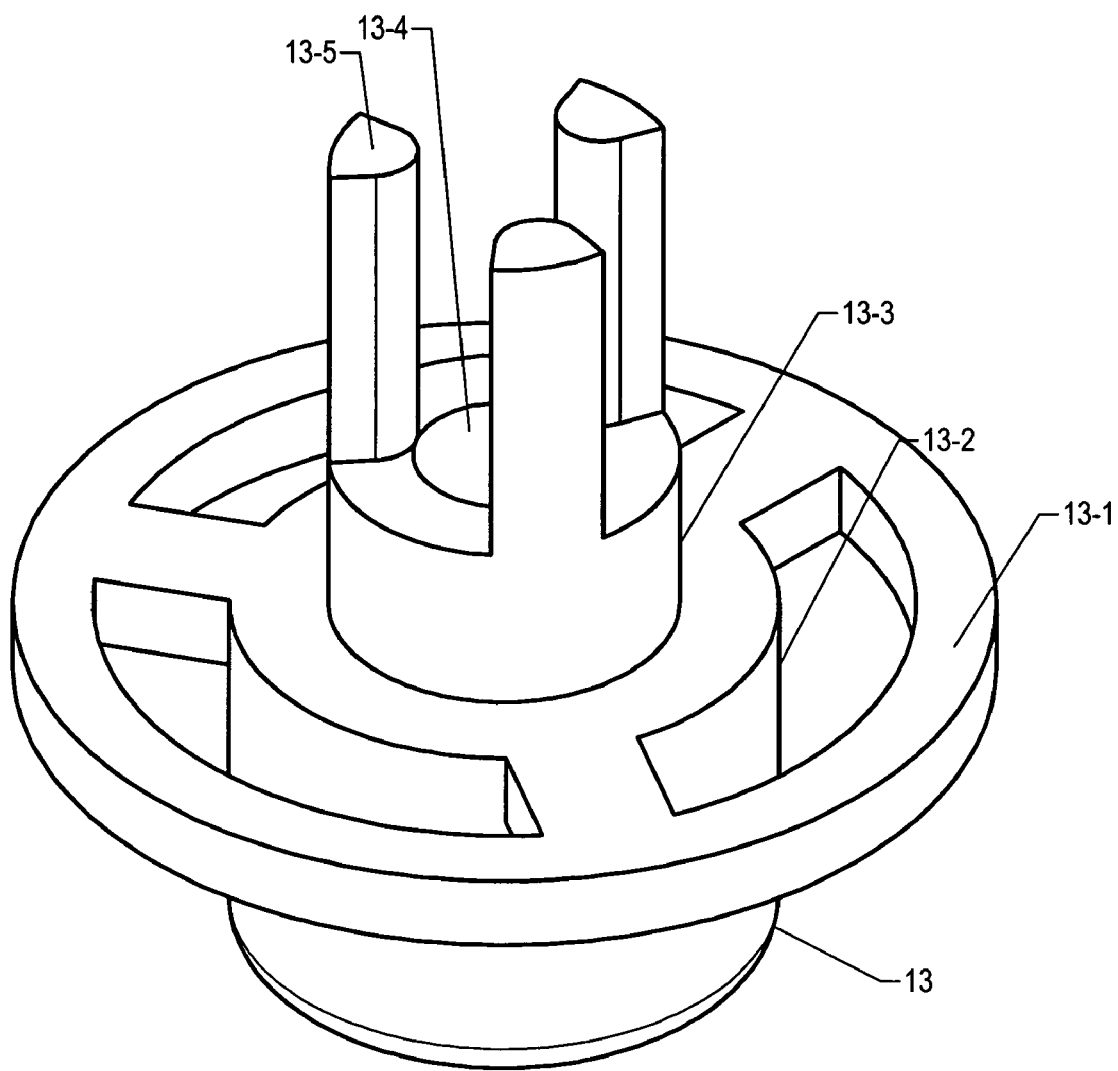

FIGS. 1A-1K show different aspects of a Type 1 valved connector 10 having a spring-actuated valve assembly, including a valve housing 13, a biasing element 12 and an introducer valve. FIG. 1A illustrates a cross-sectional view of valved connector 10 in a closed position. The valved connector 10 has a connector housing 11 wherein a biasing element 12, such as a spring, may be configured to provide a closing pressure against a valve housing 13 such that the valve assembly remains closed until a minimum threshold pressure is developed by a fluid, which may force the valve assembly open; a partial vacuum is created on the outlet side of the valved connector 11; or until a pump is actuated to open the valve assembly. Associated with the valve housing 13 are first (or lower) slit septum 14, hole septum 15 and second (or upper) slit septum 16, which together form an introducer valve with an orifice for passage of an introducer such as a guidewire. The phrases "lower septum" and "upper septum" are not meant to designate the positions of the septa relative to the valved connector. The valve assembly or valved connector 10 may optionally include a porous mesh or filter (not shown) that may be configured to filter the fluid flowing through the valved connector, while allowing access of an introducer through the valved connector 10 via the porous mesh or filter. Such a filter could, for example, be placed on top of the valve housing 13, having a central circular opening with a diameter the same as, or slightly larger than head 13-3 and an outer diameter the same as disk 13-1 (FIG. 1E). The inlet 17 to and the outlet 18 from the valved connector could be threaded or smooth without threads. As shown the inlet 17 contains threads around the outside thereof to permit locking connection to a threaded device (such as a luer fitting). A luer fitting (not shown) may be connected to the inlet 17 and a catheter (not shown) may be connected to the outlet 18.

FIG. 1B shows a cross-sectional view of valved connector 10 in the open position. The valve housing 13 is at a lower position than in FIG. 1A, the biasing element 12 being in a compressed state. In the open position, a fluid enters inlet 17, goes through the gap between upper slit septum 16 and the inside of the inlet 17, enters the space between the valve housing 13 and an interior of the connector housing 11, flows through openings in the disk portion of the valve housing (e.g., openings 13-2 in disk 13-1 of FIG. 1E), and exits the valved connector 10 through the outlet 18. FIGS. 1C and 1D are front views, respectively, of the cross-sections of the valved connector 10 shown in FIGS. 1A and 1B.

Figure 1F:
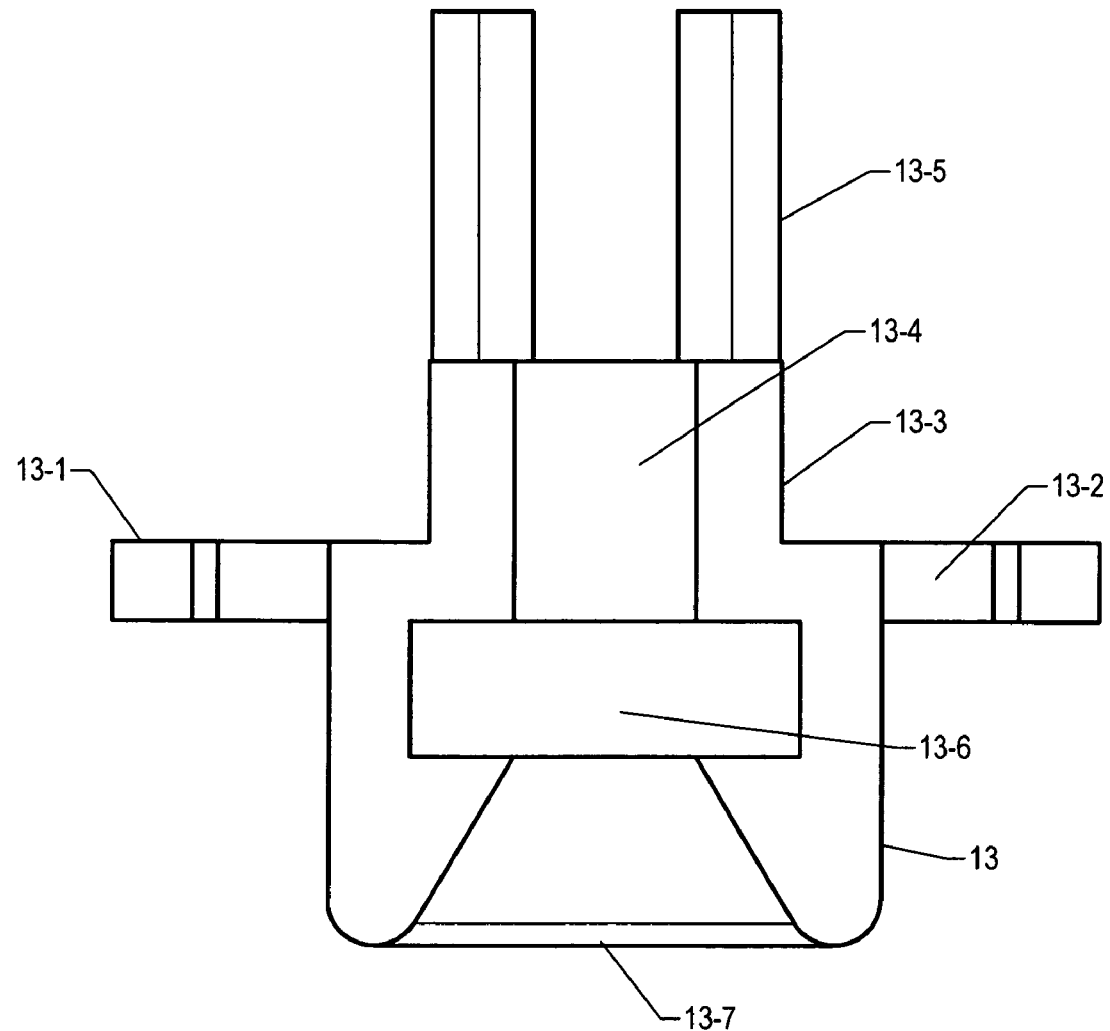
Figure 1G:
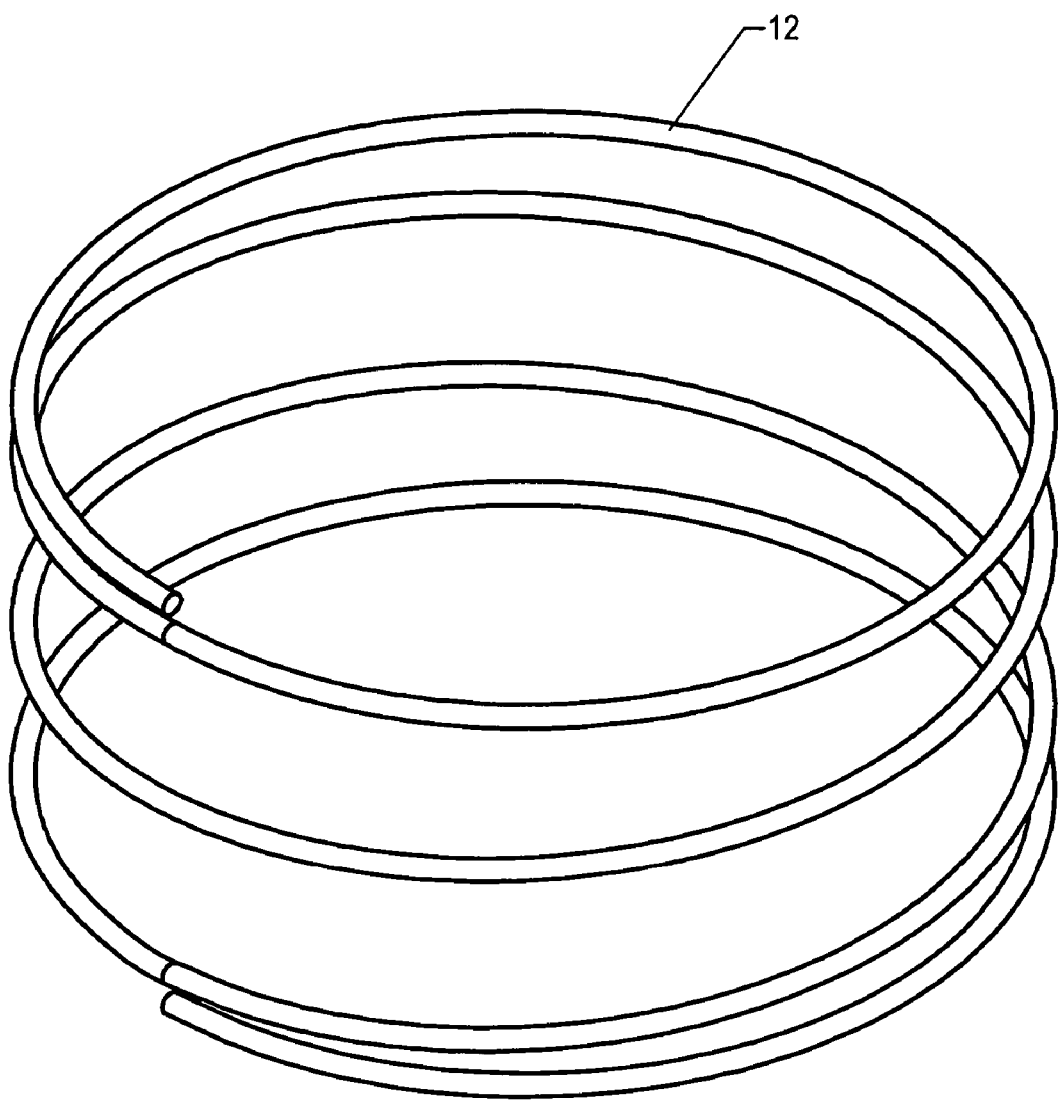
Figure 1H:
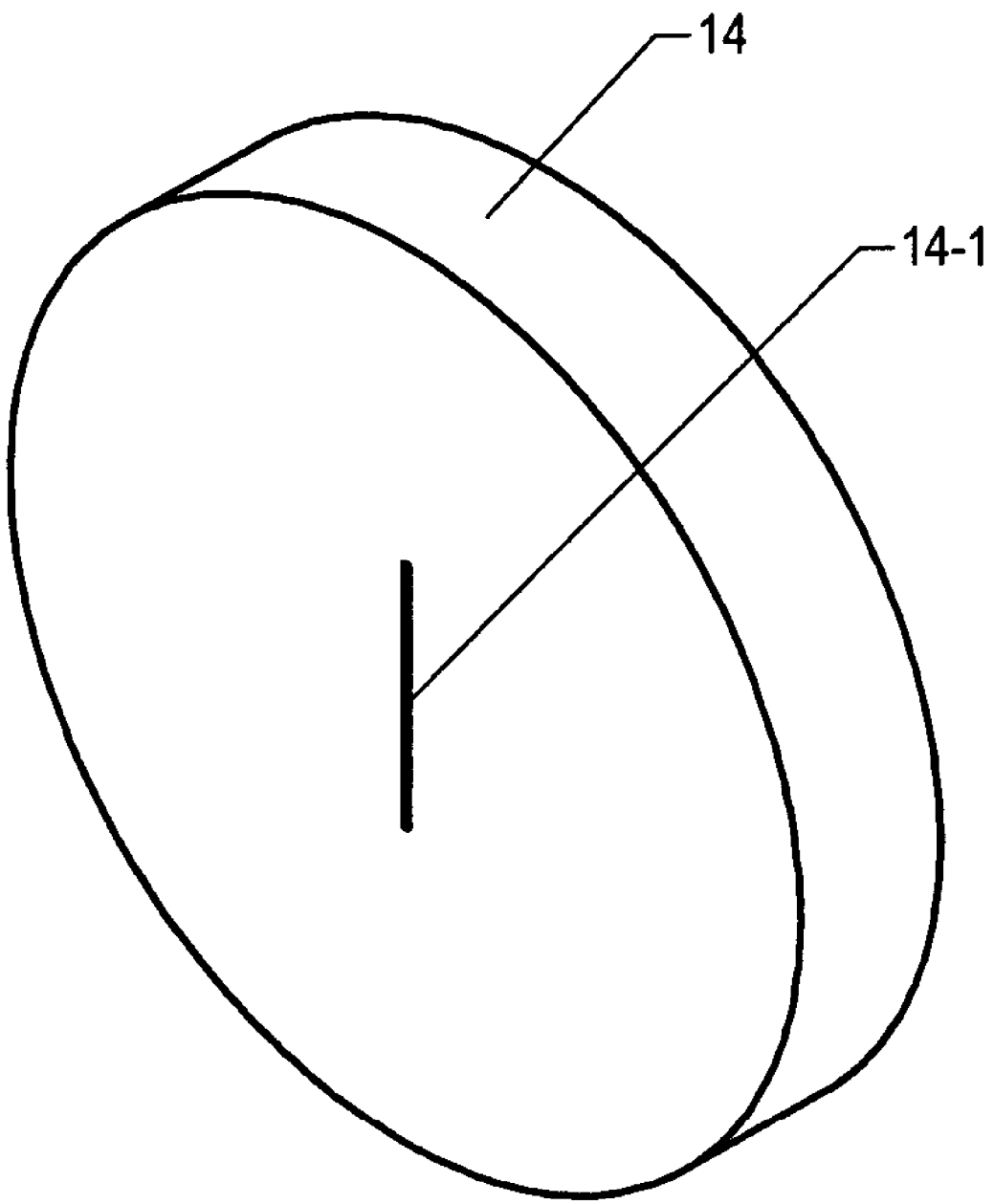
Figure 1I:
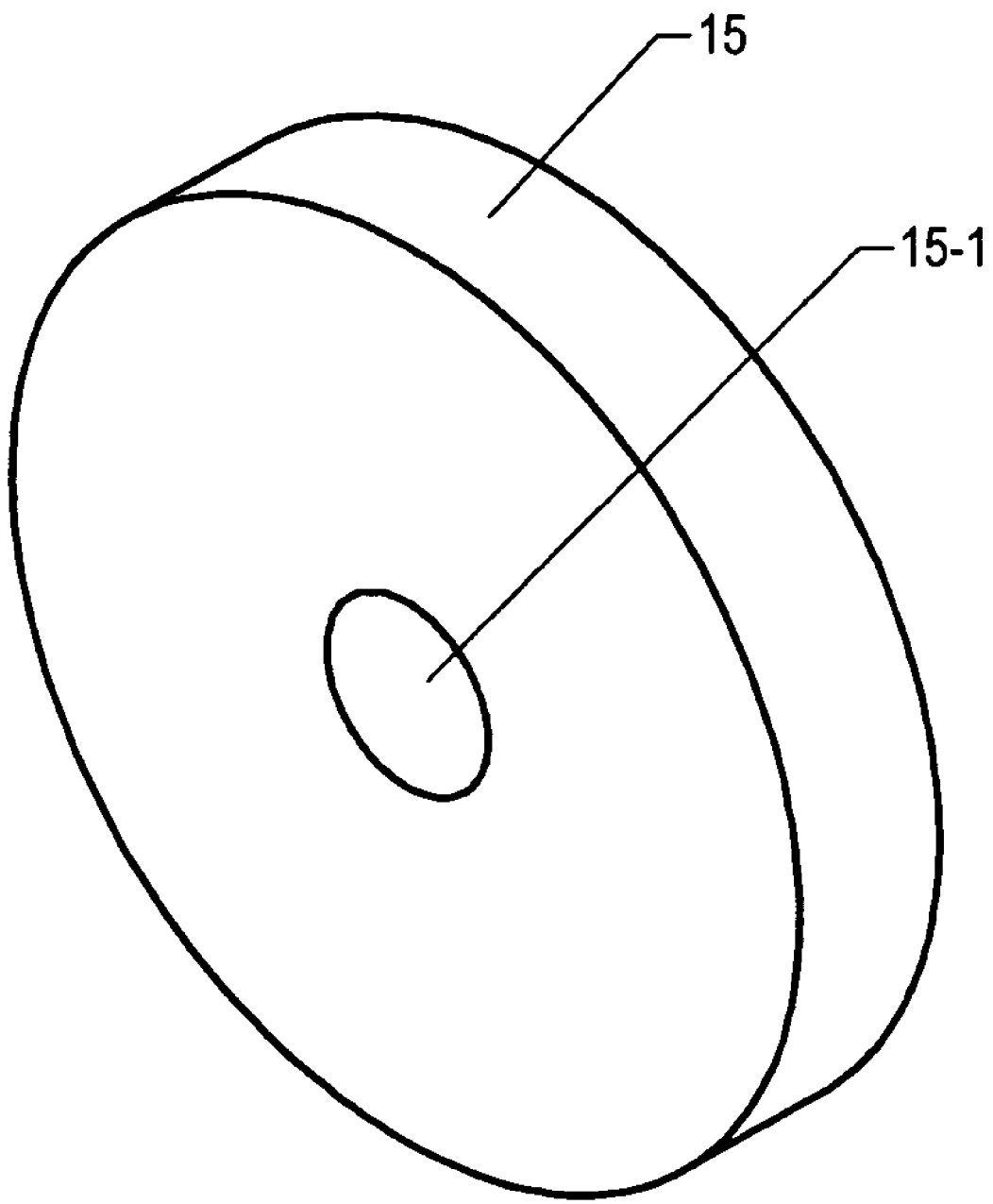
Figure 1J:
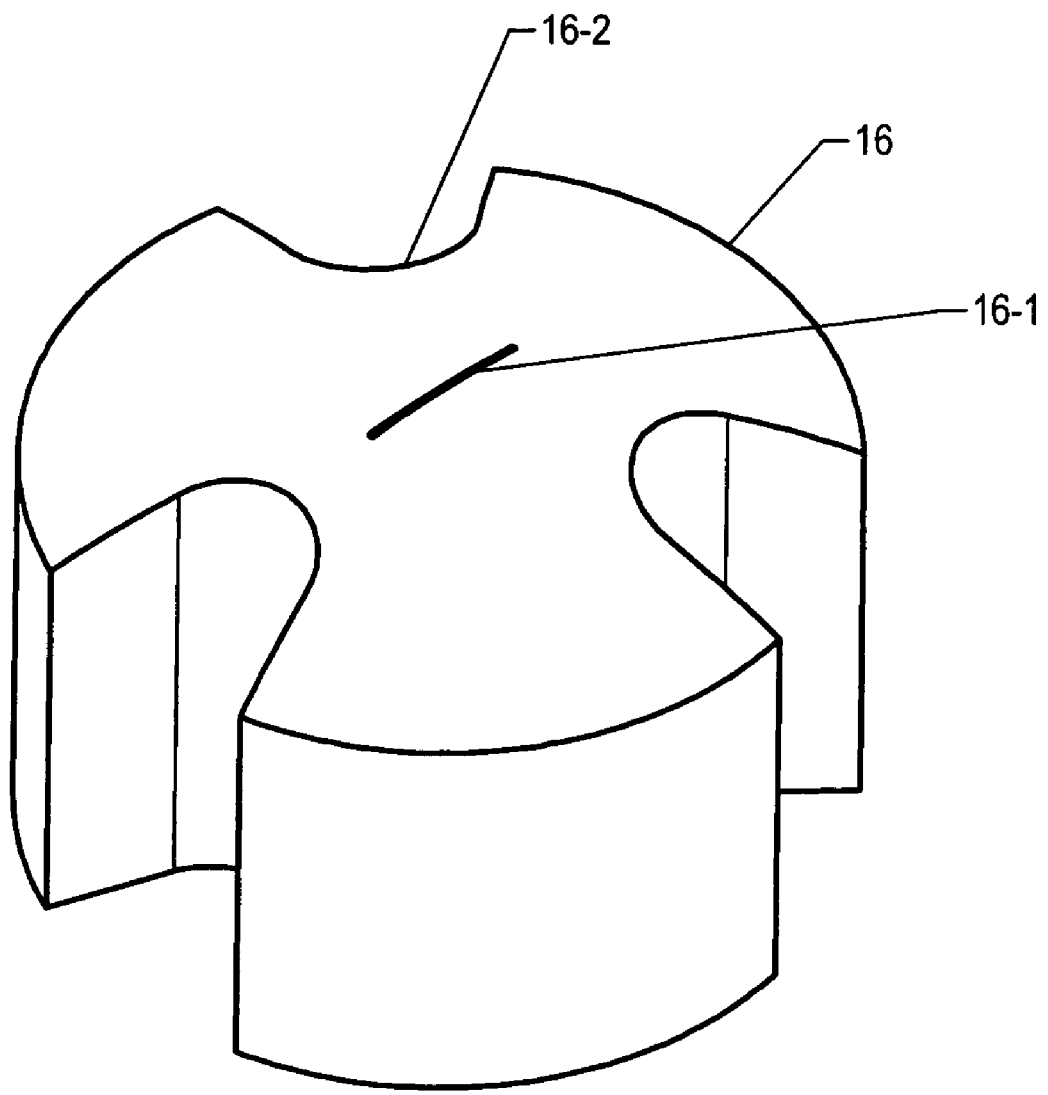
Figure 1K:
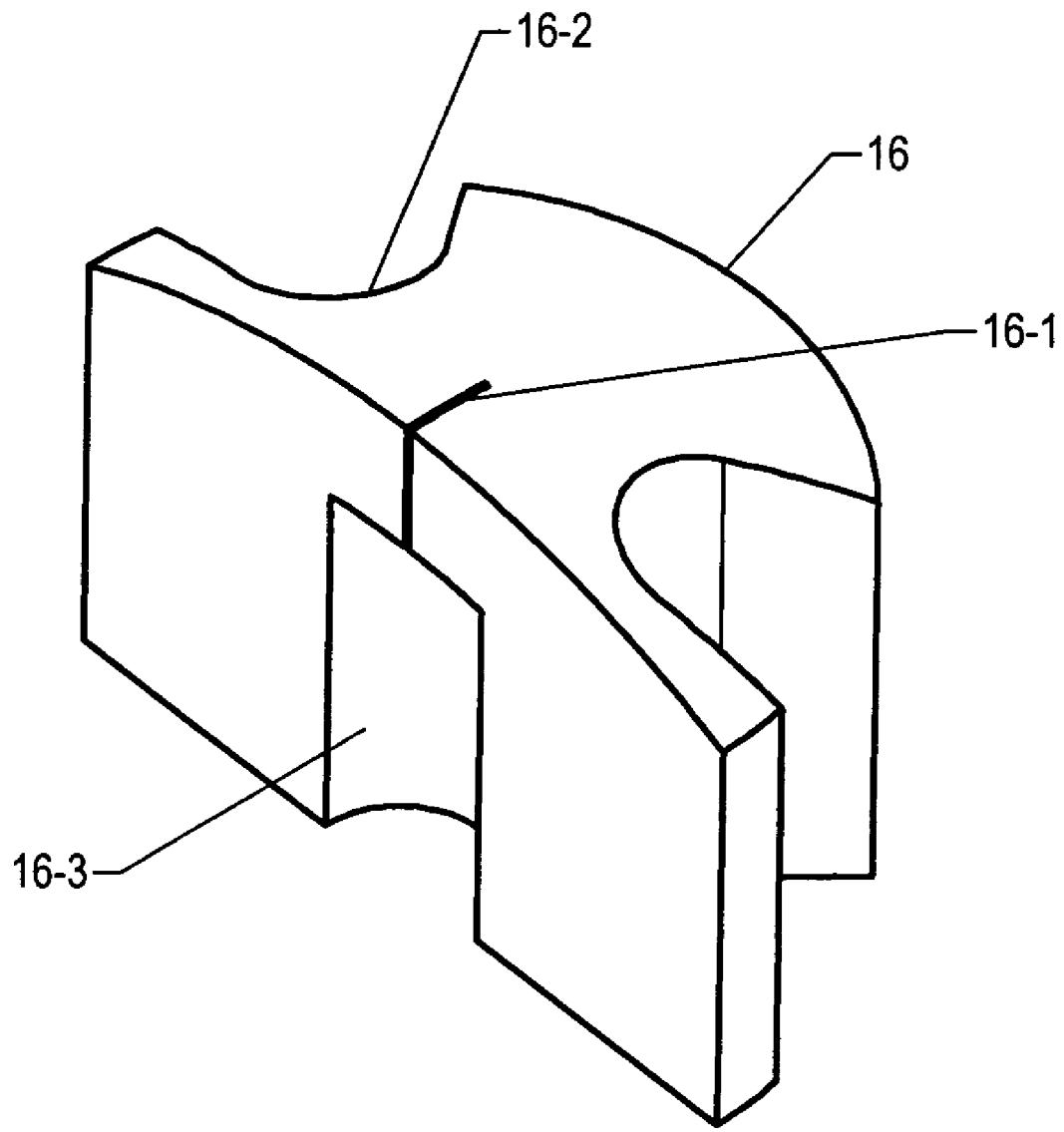

FIG. 1E shows a detailed view of the valve housing 13, which has a disk 13-1 with openings 13-2 therein, a head 13-3 having protrusions 13-5 and an outlet (or lower) portion (shown as 13-7 in FIG. 1F). The valve housing 13 has a central bore 13-4 traversing through the length thereof. FIG. 1F shows the front view of a cross-sectional view of the valve housing 13. The front view shows a cavity 13-6 within the valve housing 13 for holding the lower slit septum 14 and hole septum 15. The upper slit septum 16 is mounted between the protrusions 13-5. FIG. 1G shows one embodiment of the biasing element, i.e., a spring 12. FIG. 1H shows the lower slit septum 14 with the slit 14-1. FIG. 1I shows the hole septum 15 having a hole 15-1. FIG. 1J shows the upper slit septum 16 having a slit 16-1 and recessed portions 16-2 where the protrusions 13-5 would be positioned when the slit septum 16 is placed over the head 13-3 of the valve housing 13. FIG. 1K shows a cross-section of the upper slit septum 16 showing a bore 16-3 within the upper slit septum 16 below the slit 16-1.

FIGS. 2A-2I show different aspects of another Type 1 valved connector, valved connector 20, having a spring-actuated valve assembly. The differences between valved connector 10 and valved connector 20 are primarily in the design of the valve assembly. In particular, the middle of the upper septum 26 is shaped as an inverted cup shaped dome that is at least partially enclosed by the head of the valve housing 23. In addition, the protrusions 23-5 on the head of the valve housing 23 are shorter in length than those of valved housing 13. Also, the protrusions 23-5 in this example are bowl-shaped within the center of the protrusions.

Figure 2A:
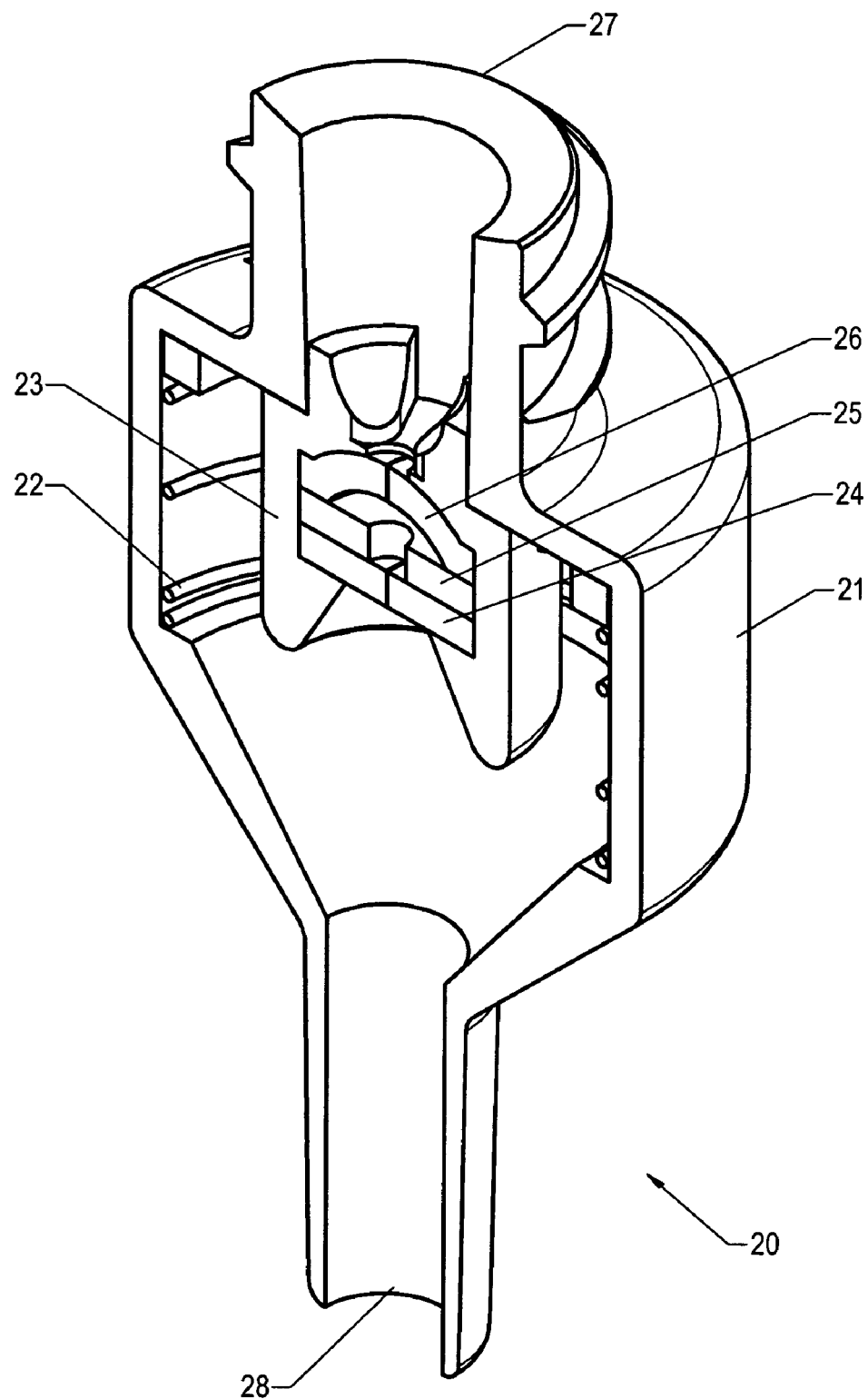
FIGS. 2A-2I illustrate different aspects of another valved connector according to the present invention.

FIG. 2A shows a cross-section of a spring-actuated valved connector 20 in a closed position. The valved connector has a connector housing 21 wherein a biasing element 22, such as a spring, may be configured to provide a closing pressure against the valve housing 23 such that the valve assembly remains closed until a minimum threshold pressure is developed by a fluid, which may force the valve assembly open; a partial vacuum is created at the outlet side of the valved connector 20; or until a pump is actuated to open the valve assembly. Associated with the valve housing 23 are first (or lower) slit septum 24, hole septum 25 and second (or upper) slit septum 26, which together form an introducer valve with an orifice for passage of an introducer such as a guidewire. The valve assembly or valved connector 20 may optionally include a porous mesh or filter (not shown) that may be configured to filter the fluid flowing through the valved connector 20, while allowing access through of an introducer through the valved connector via the porous mesh or filter. The inlet 27 to and the outlet 28 from the valved connector 20 could be threaded or smooth without threads. A luer fitting (not shown) may be connected to the inlet 27 and a catheter (not shown) may be connected to the outlet 28.

Figure 2B:
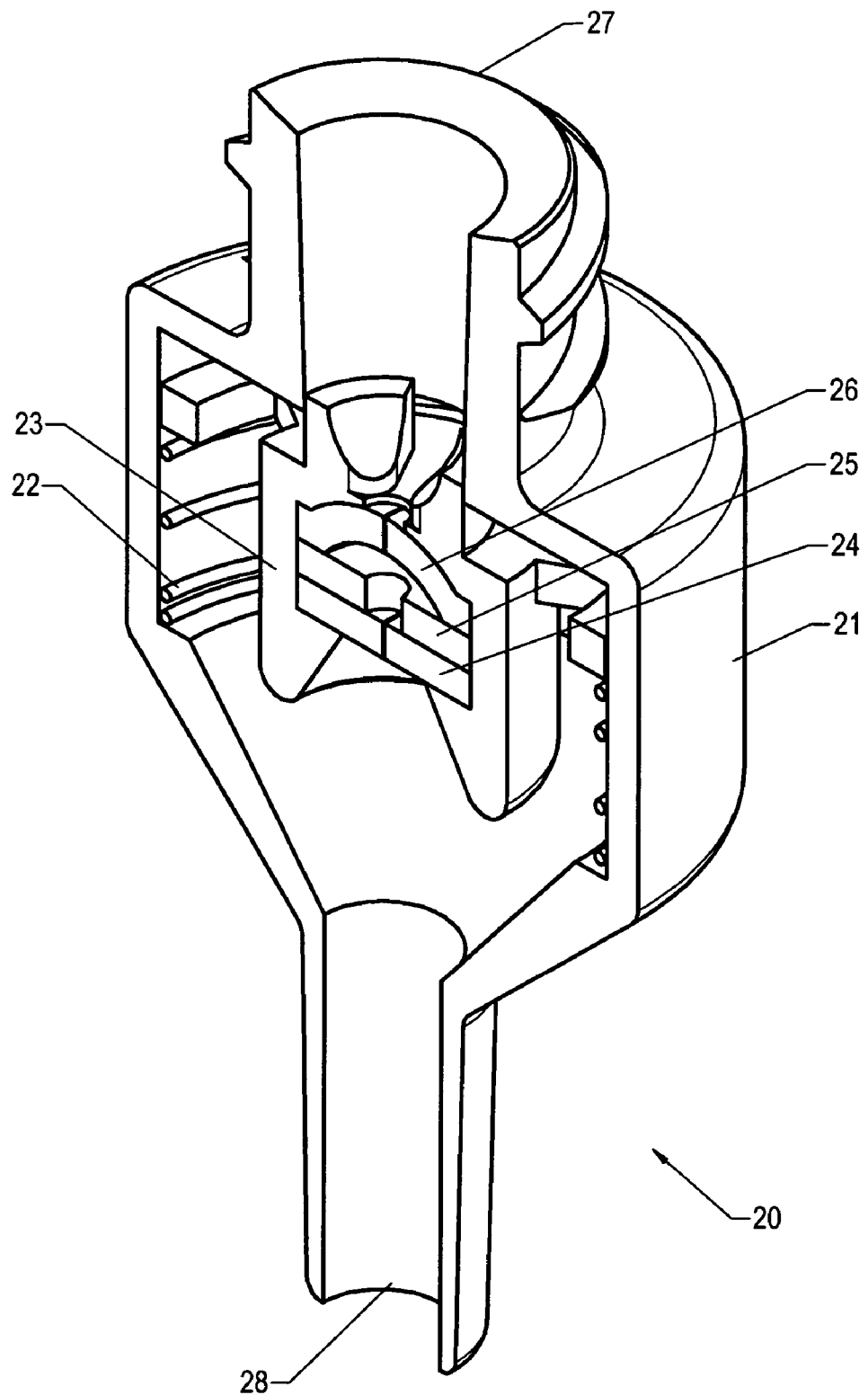
Figure 2C:
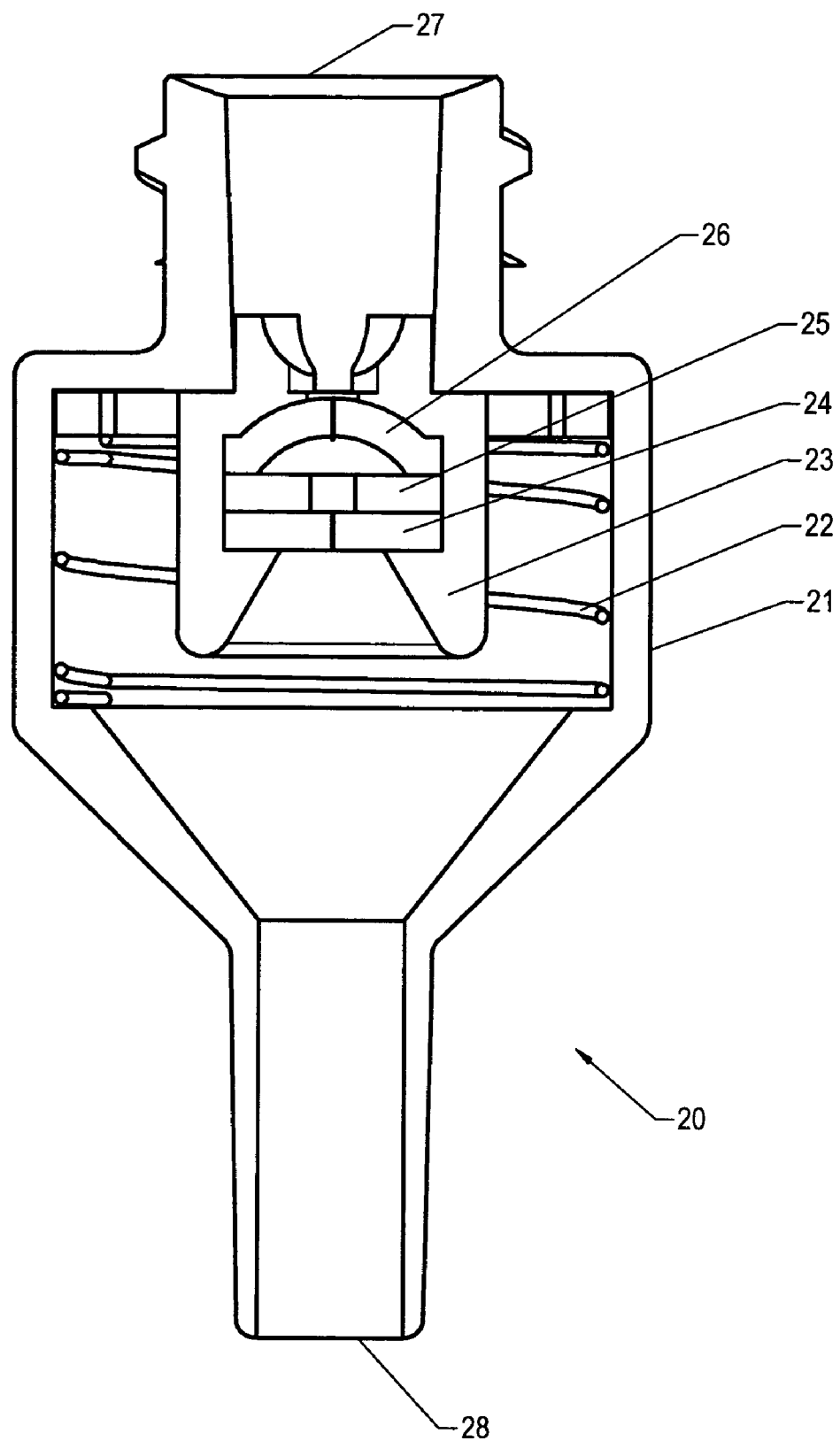
Figure 2D:
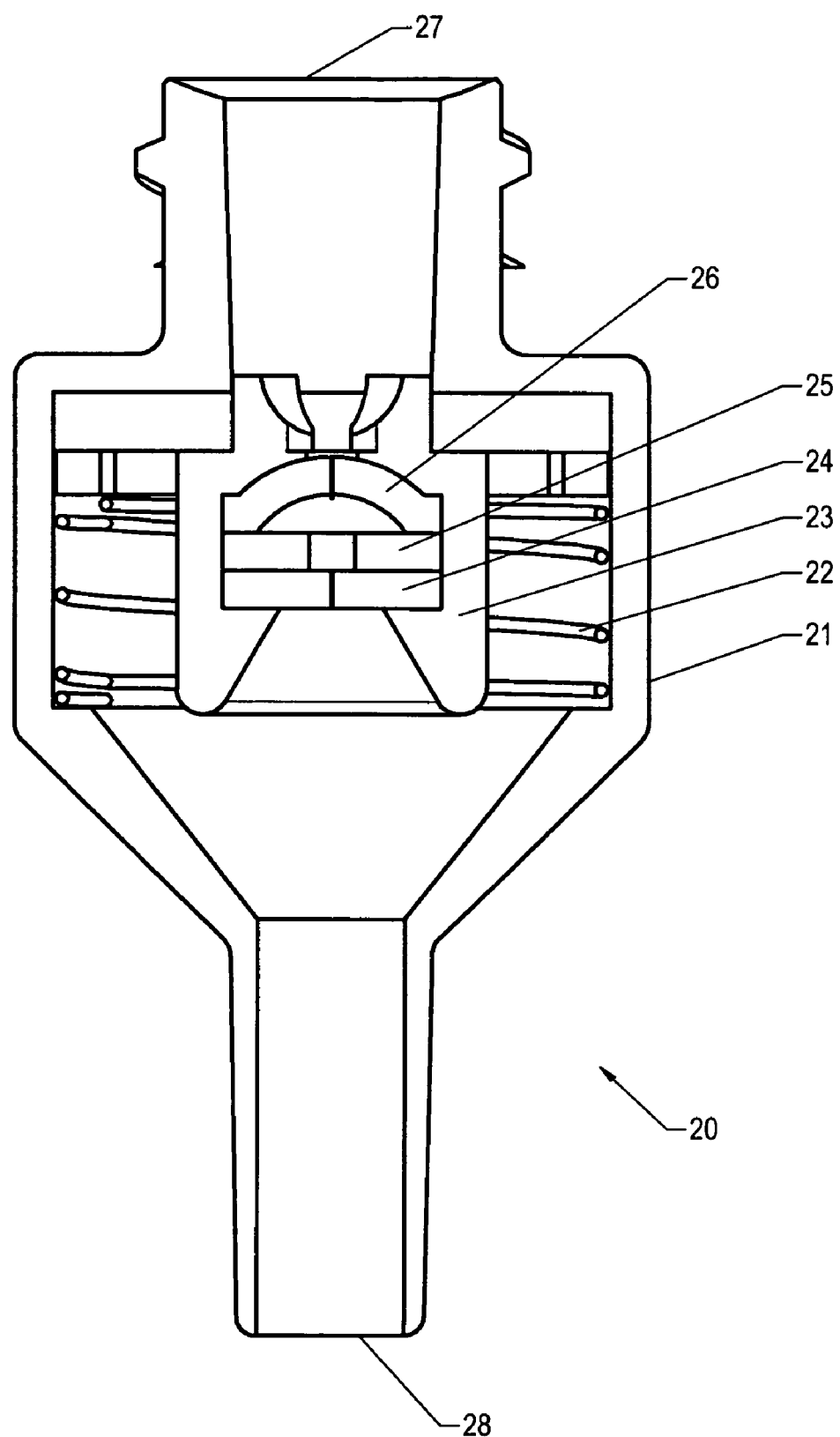

FIG. 2B shows a cross-section of the spring-actuated valved connector 20 in an open position. The valve housing 23 is at a lower position than in FIG. 2A, the biasing element 22, such a spring, being in a compressed state. In the open position, a fluid enters inlet 27, goes through the gap between the top of the valve housing 23 and the inside of the inlet 27, enters the space between the interior of the connector housing 21 and the valve housing 23, flows through openings in the disk portion of the valve housing (e.g., openings 23-2 in disk 23-1 of FIG. 2E), and exits the valved connector 20 through the outlet 28. FIGS. 2C and 2D are front views, respectively, of the cross-sections of the valved connector 20 shown in FIGS. 2A and 2B.

Figure 2E:
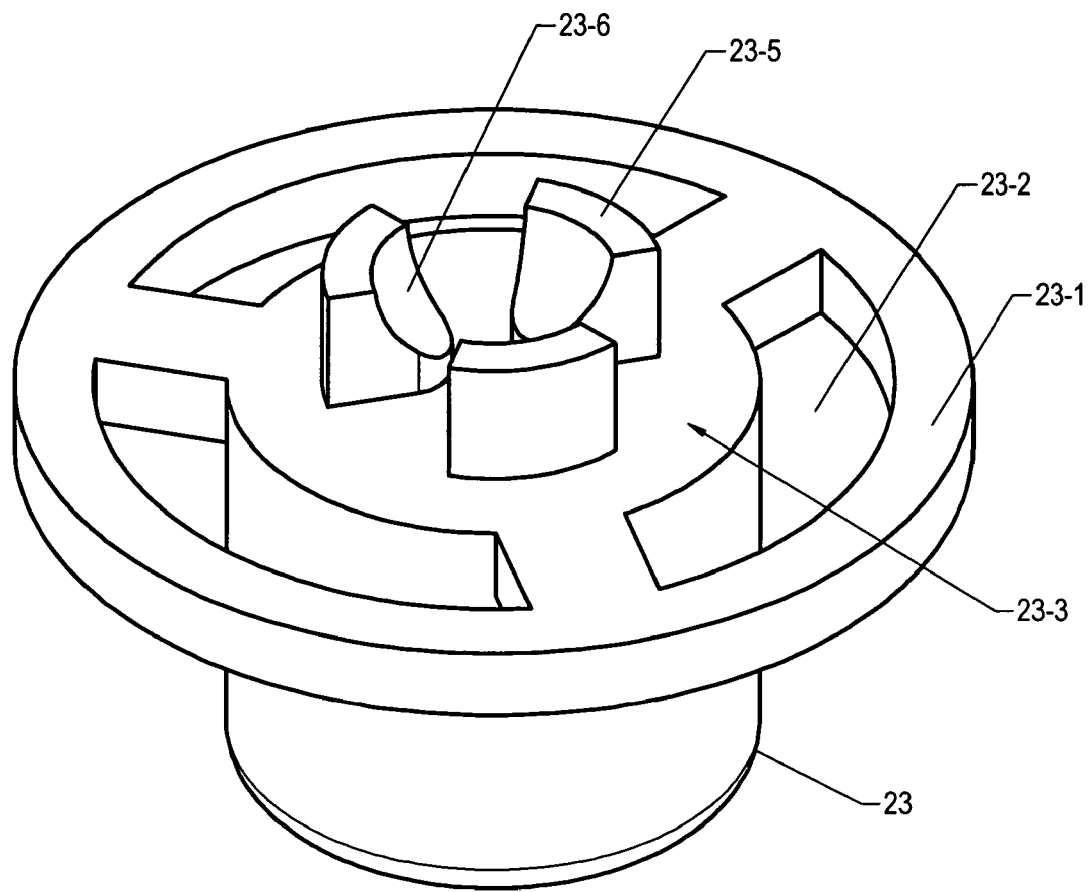
Figure 2F:
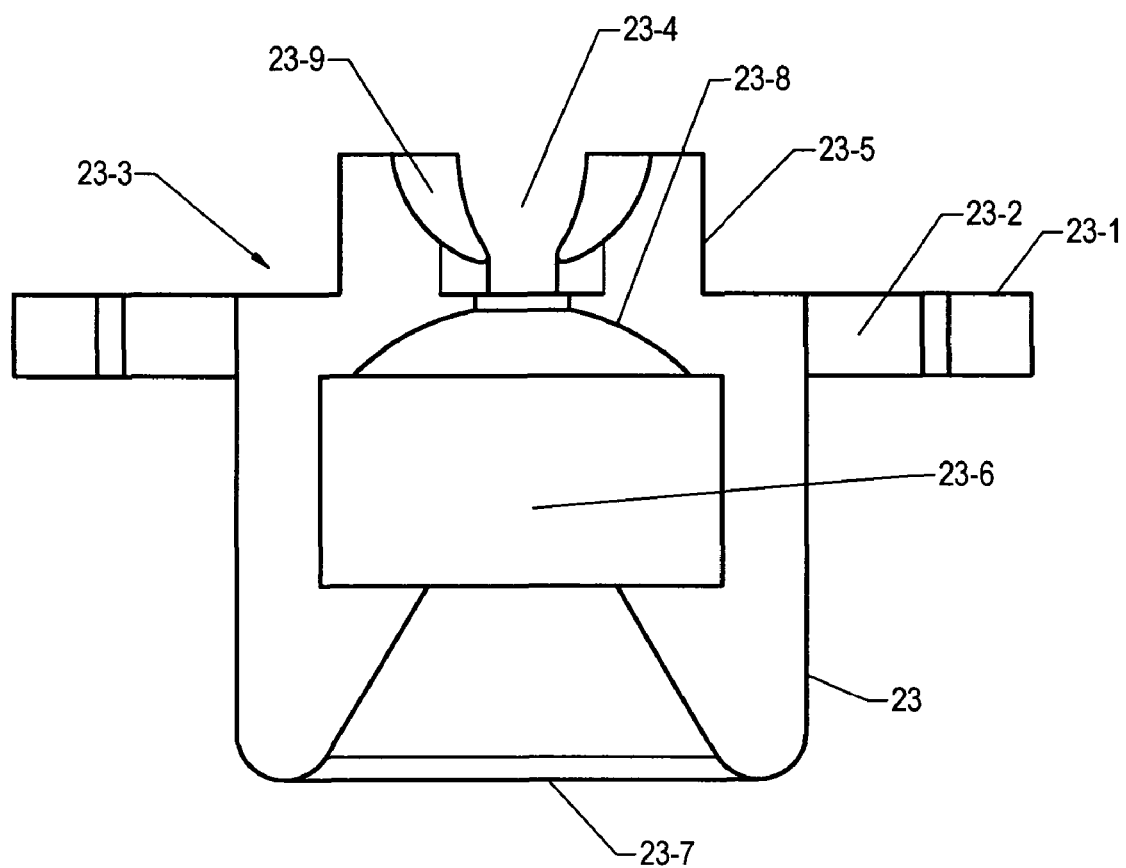
Figure 2G:
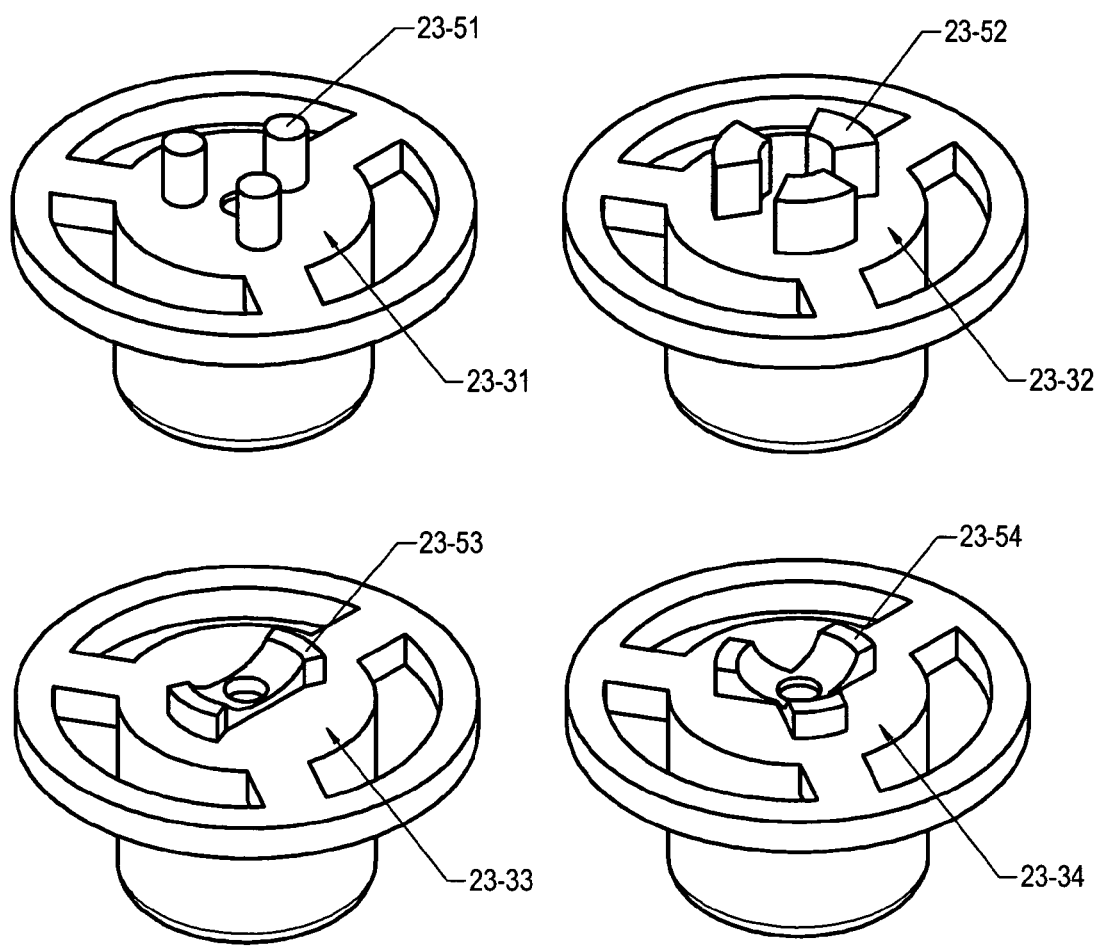
Figure 2H:
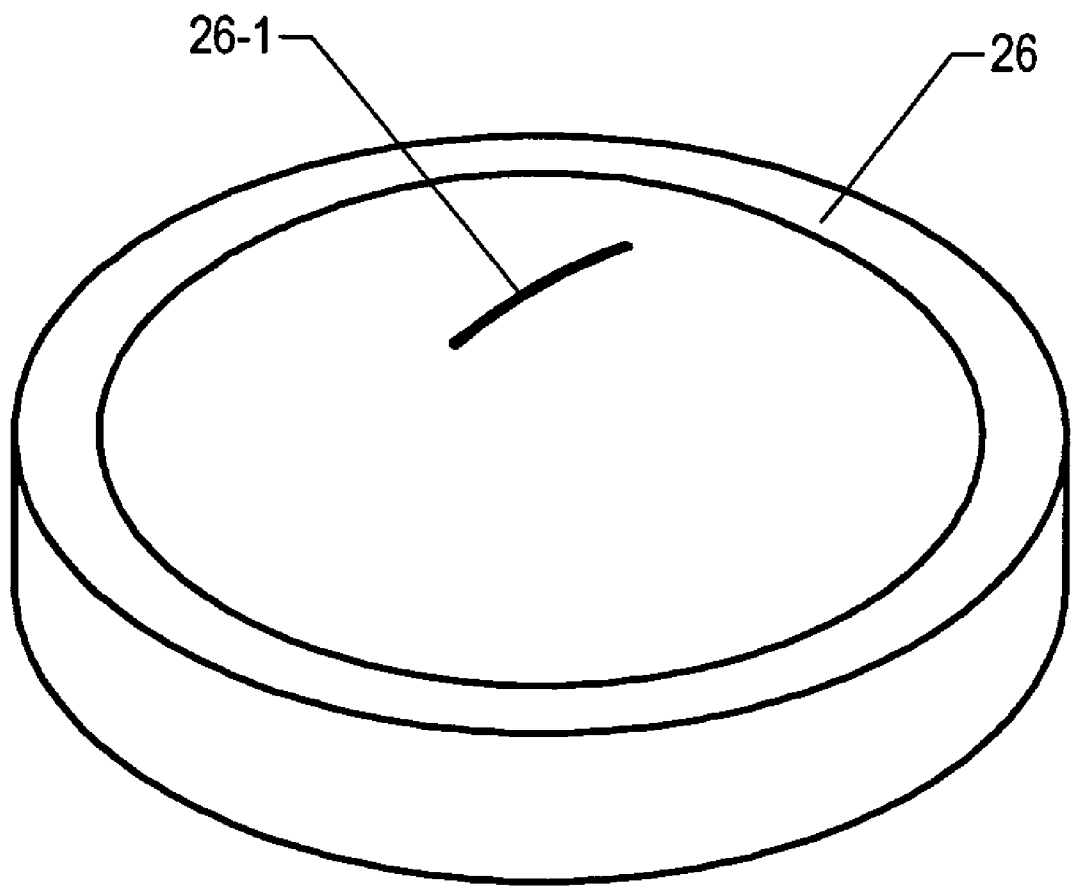
Figure 2I:
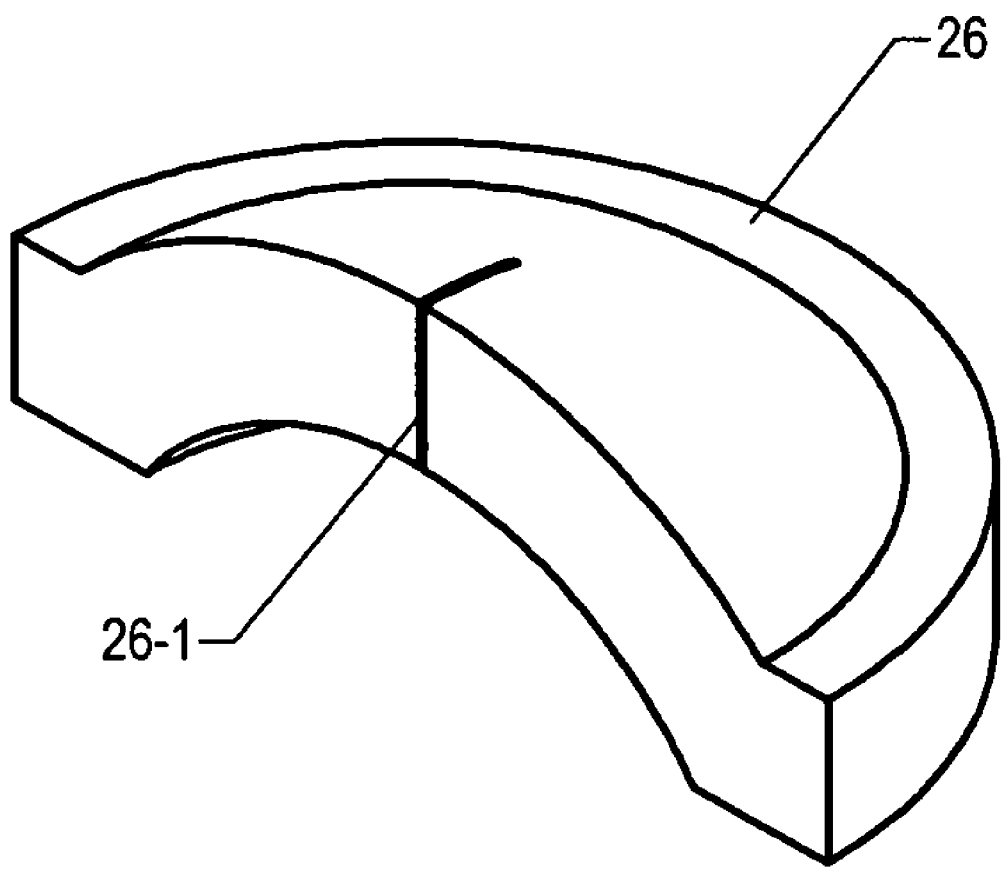

FIG. 2E shows a detailed view of the valve housing 23, which has a disk 23-1 with openings 23-2 therein, protrusions 23-5 and an outlet (or lower) portion (shown as 23-7 in FIG. 2F). The protrusions 23-5 have inwardly directed faces 23-9, which are collectively shaped in the form of a bowl within the core of the protrusions. As shown in FIG. 2F, the valve housing 23 has a central bore 23-4 traversing through the length thereof. FIG. 2F shows the front view of a cross-section of the valve housing 23. The front view shows a cavity 23-6 within the valve housing 23 for holding the lower slit septum 24 and hole septum 25. The upper slit septum 26 is mounted between the protrusions 23-5. FIG. 2G shows different embodiments of the head 23-3 (designated 23-31, 23-32, 23-33 and 23-34) and protrusions 23-5 (designated 23-51, 23-52, 23-53 and 23-54) of the valve housing 23. FIG. 2H shows the upper slit septum 26 having the slit 26-1 and the dome thereof. The dome would be positioned under the head 23-3 of the valve housing 23. FIG. 2I shows a cross-section of the upper slit septum 26, showing the dome of the upper slit septum 26 with the slit 26-1 therein.

Figure 3A:
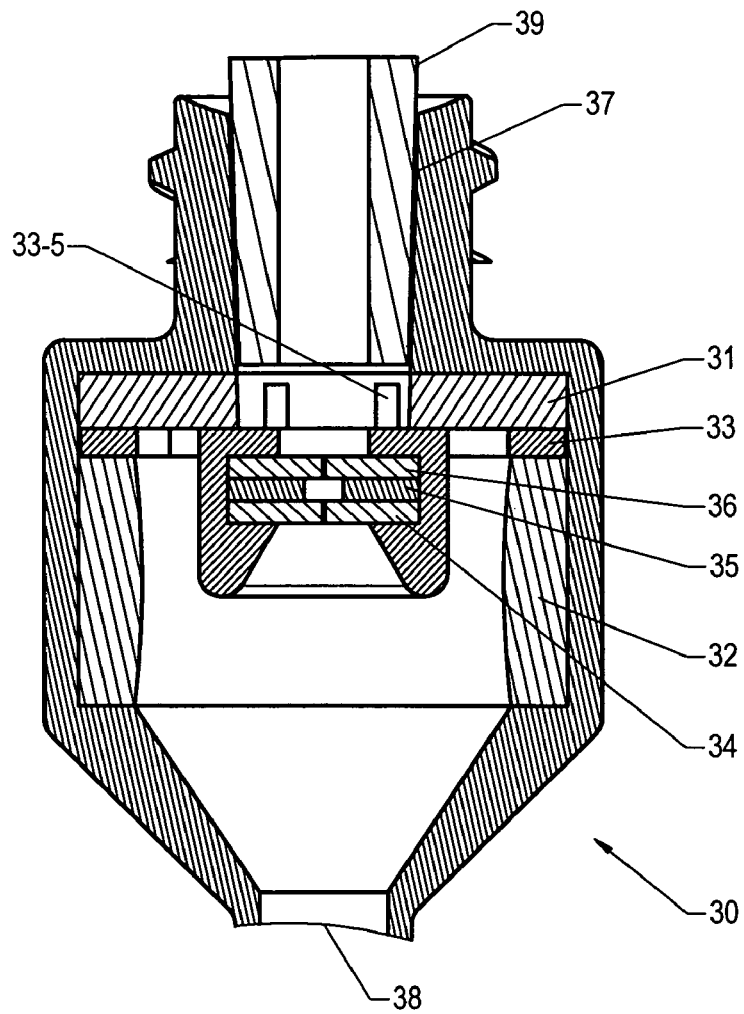
FIG. 3 illustrates yet another valved connector according to the present invention.
Figure 3B:
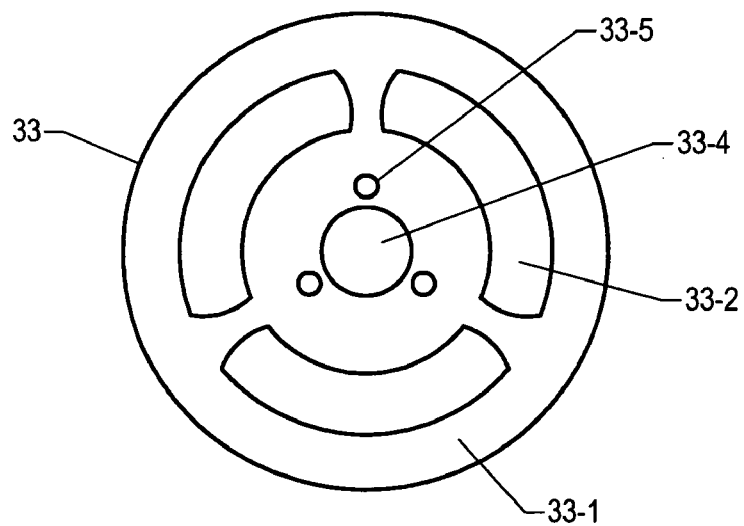

FIG. 3 shows a Type 1 valved connector having a compression ring actuated valve assembly. FIG. 3A shows a valved connector 30 having a valve assembly, comprising biasing elements 31 and 32, which are shown as rubbery compression rings (e.g., O rings), and a valve housing 33 seated between the biasing elements 31 and 32. Biasing element 31 provides a seal to the valved connector 30 in a closed position and biasing element 32 acts to bias the valved connector in the closed position such that valve housing 33 is pressed against biasing element 31. Located within the valve housing 33 are lower slit septum 34, hole septum 35 and upper slit septum 36 that together form an introducer valve. The valved connector 30 has an inlet 37, sized to receive a luer fitting 39, and an outlet 38. As shown in FIG. 3B, the valve housing 33 has a disk 33-1 with openings 33-2 therein, protrusions 33-5 and has a bore 33-4 traversing through the length thereof.

The valve assembly remains closed until a minimum threshold pressure is developed by a fluid; a partial vacuum is created at the outlet side of the valved connector; the luer fitting pushes on the protrusions 33-5, which may force the valve assembly open; or until a pump is actuated to open the valve assembly. The valve assembly or valved connector 30 may optionally include a porous mesh or filter (not shown) that may be configured to filter the fluid flowing through the valved connector 30, while allowing access of an introducer through the valved connector via the porous mesh or filter. The inlet 37 to and the outlet 38 from the valved connector could be threaded or smooth without threads.

Figure 4A:
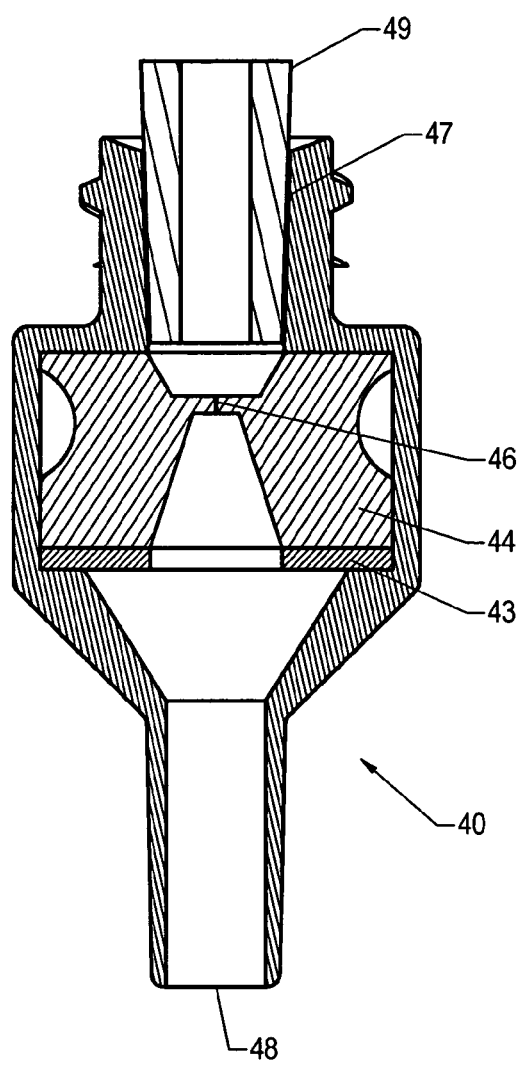
FIGS. 4A and 4B illustrate yet another valved connector according to the present invention.
Figure 4B:
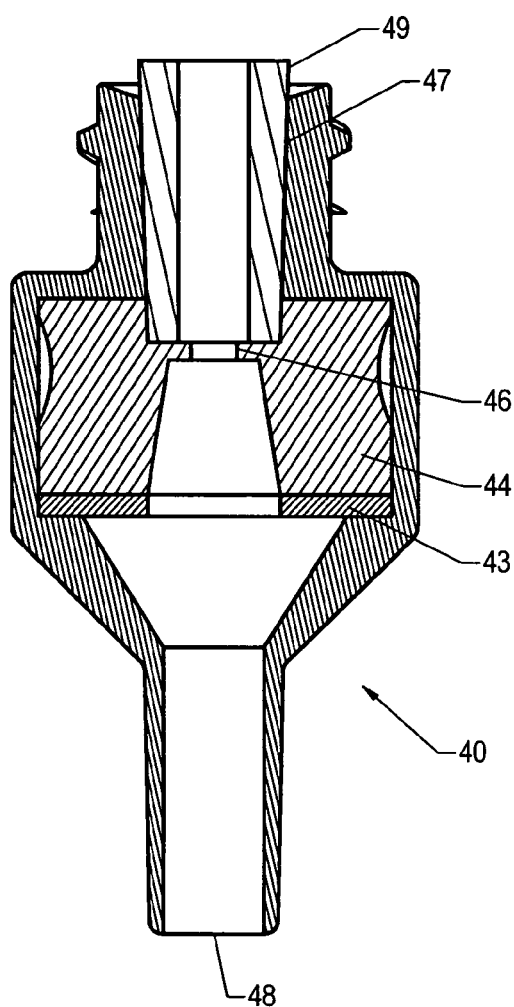

FIGS. 4A and 4B illustrate a Type 1 valved connector having a flexible valve element on a support disk. These figures show a valved connector 40 having a valve assembly, comprising a support disk 43 and a valve element 44. The valve element 44 is a slit valve with slit 46, valve element 44 having an upper open portion and lower open portion. The valve element 44 may be made of a material, such as silicone, that is soft enough to permit introduction of a guidewire through the slit 46 while providing a seal therearound. The valve element 44 rests on top of support disk 43, which itself is positioned on top of a funnel shaped outlet at the base of the valved connector. The valved connector 40 has an inlet 47, sized to receive a luer fitting 49, and an outlet 48. The inlet 47 to and the outlet 48 from the valved connector could be threaded or smooth without threads. The valve assembly remains closed until a minimum threshold pressure is developed by the fluid, a partial vacuum is created at the outlet side of the valved connector, or until the luer fitting 49 enters the upper open portion of the valve element 44 and contacts the valve element 44, forcing the sides of the valve element 44 toward the walls of the valved connector housing, which open the slit 46 as shown in FIG. 4B. As can be seen in FIGS. 4A and 4B, the support disk acts to prevent movement of the valve element 44 downward inside the housing of the valved connector 40 as the base of the valve element 44 is wider than the shoulder on which the support disk 43 is positioned.

Figure 5A:
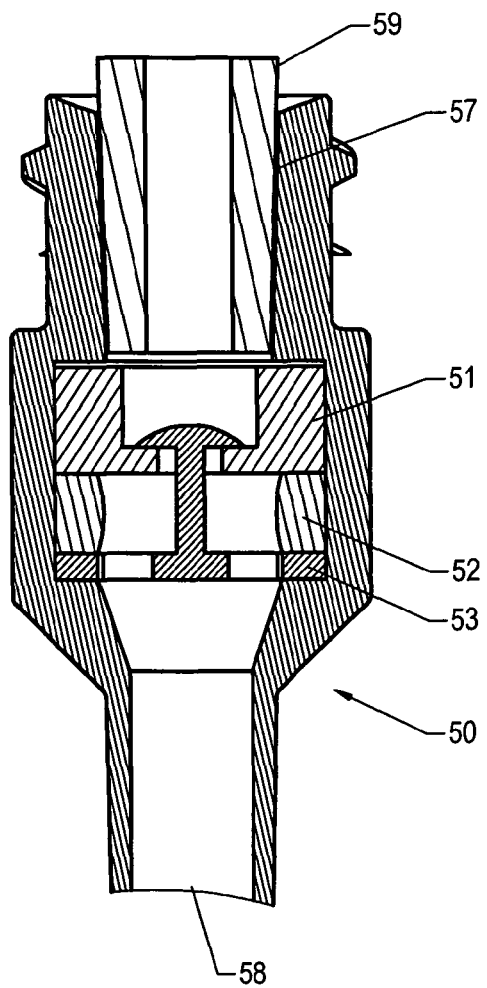
FIGS. 5A-5E illustrate another valved connector according to the present invention.
Figure 5B:
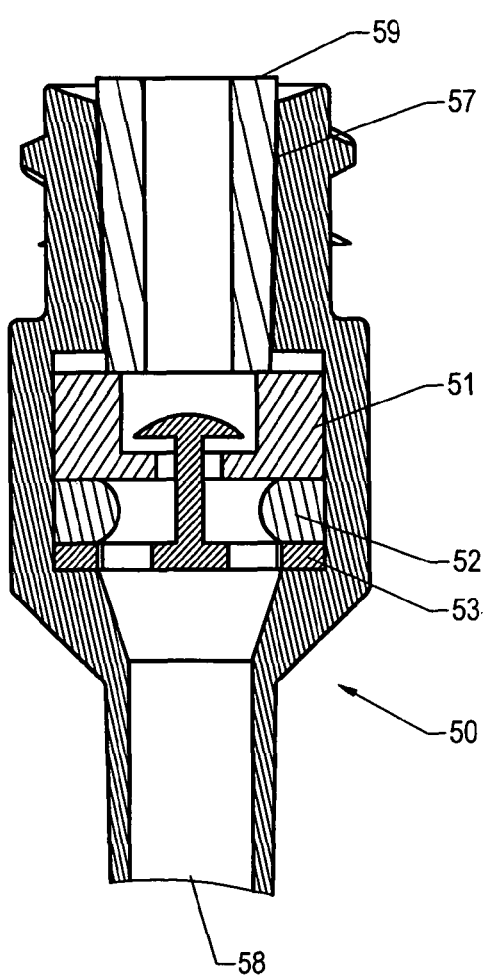
Figure 5C:
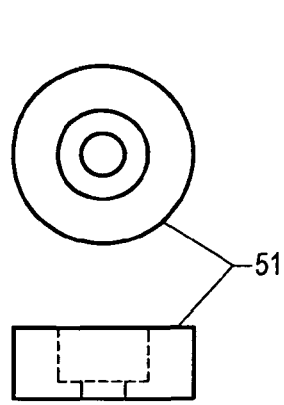
Figure 5D:
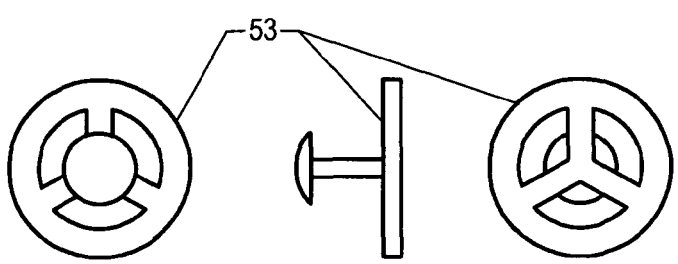
Figure 5E:
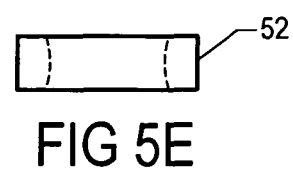

FIGS. 5A-5E show a Type 2 valved connector 50, which includes a valve assembly comprising a flow-through disk 53, a biasing element 52, such as a compression ring, and a sealing device 51 shaped like a sliding cylinder. The valved connector 50 has an inlet 57, sized to receive a luer fitting, and an outlet 58. The inlet 57 to and the outlet 58 from the valved connector could be threaded or smooth without threads. The flow-through disk 53 remains closed until a fluid at the inlet 57 develops a minimum threshold pressure, a partial vacuum created at the outlet side of the valved connector, or until the luer fitting pushes on the sealing device 51. As shown in FIG. 5B, as luer fitting 59 presses against sealing device 51, the biasing element 52 is compressed and a gap is created between the bottom of the sealing device 51 and the head of the flow-though disk 53. Fluid is then permitted to flow through the created gap and exits the valved connector 50 through the outlet 58. FIG. 5C illustrates sealing device 51 from a top and side view, while FIG. 5D illustrates flow-through disk 53 from a top, bottom and side view. FIG. 5E illustrates biasing element 52 from a side view.

Figure 6A:
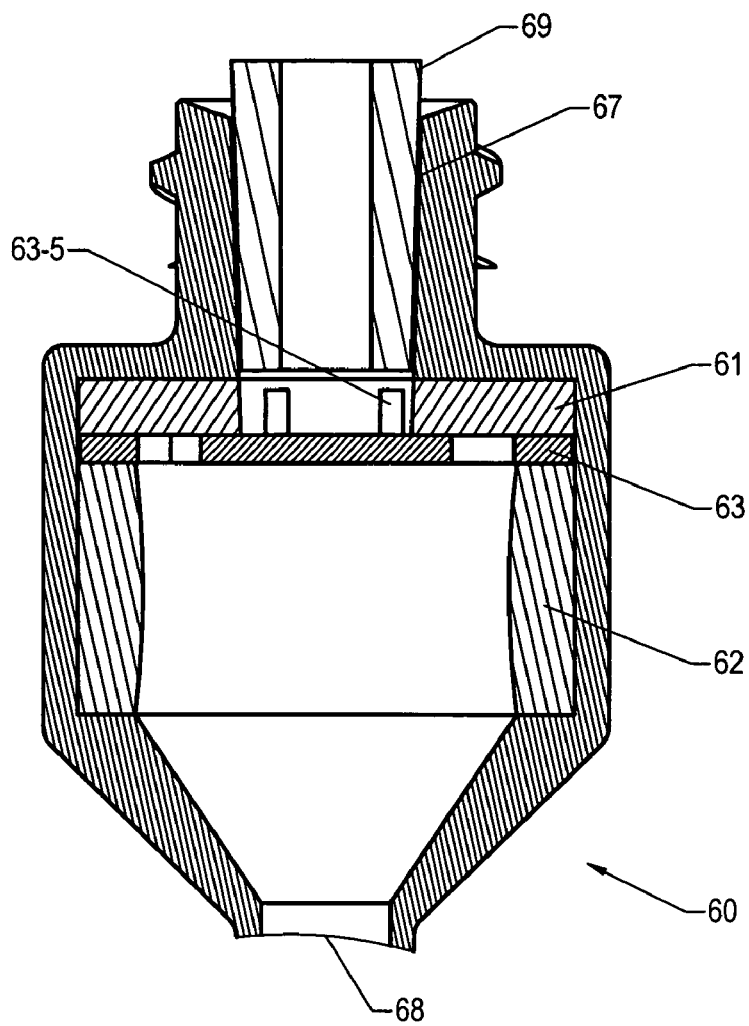
FIGS. 6A and 6B illustrate yet another valved connector according to the present invention.
Figure 6B:
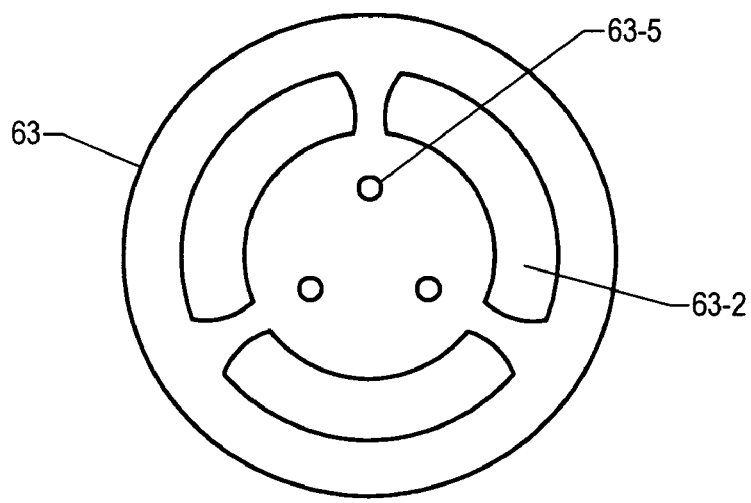

FIGS. 6A and 6B illustrate a Type 2 valved connector 60, which includes a valve assembly comprising a flow-through disk 63, a biasing element 62, such as a compression ring, and a sealing device 61 shaped like a rubbery or rigid sliding cylinder or a compression ring. The valved connector 60 has an inlet 67, sized to receive a luer fitting 69, and an outlet 68. The inlet 67 to and the outlet 68 from the valved connector could be threaded or smooth without threads. The flow-through disk 63 remains closed until a fluid at the inlet 67 develops a minimum threshold pressure, a partial vacuum created at the outlet side of the valved connector 60, or until the luer fitting 69 pushes on the protrusions 63-5 of the flow-through disk 63. Pushing on the protrusions 63-5 compresses the biasing element 62 and creates a gap between the bottom of the sealing device 61 and the top surface of the flow-though disk 63. The fluid then flows through the created gap, through the openings 63-2 of the flow-through disk 63 (FIG. 6B) and exits the valved connector 60 through the outlet 68.

The device of this invention is a valve assembly designed to be small enough to fit inside a modified luer connectable hub of a catheter assembly or as an attachable valved connector fitting. The valve assembly provides functional advantages over current valve assemblies. The valve is designed for repeated and/or prolonged access with no added restriction to fluid flow in either direction. One type of the device includes an additional introducer valve that allows passage of and seals around an introducer such as a guidewire or small diameter tube that is inserted through the device. The additional valve prevents fluid or air leakage when the device is being accessed with an introducer such as a guidewire or small diameter tubing without opening the primary valve assembly. Use would be indicated where venous access with unrestricted fluid flow and multiple accesses are required such as dialysis catheters. Additionally, Type 1 devices would be indicated when the catheter is placed or replaced using an "over the guidewire" technique or when the device is accessed with a small diameter tube and sealing is indicated to prevent fluid loss or air embolism.

The valve assembly may be designed to be small enough to fit within a cylindrical housing with maximum dimensions of 0.5" diameter and 1.0" length that includes a female luer fitting at one end and a tube (catheter) fitting at the other end. The secondary valve is a soft material (i.e., silicone 50-60 Shore A) designed to allow the passage of and seal around a guidewire or tube 0.030" to 0.060" diameter. The valve may also be designed to be incorporated within a small housing that is compatible with multiple fittings, i.e., luer lock, slip fit, compression, etc. Valve function or performance is not affected by the addition of color or clear housing/components. Component or housing components are not affected by opacity or color. Markings and scales could be used on an as needed basis per application. Device function is not integrally linked to markings, etc. Moreover, the device of the present invention is sterilizable using standard techniques (EtO, gamma, etc.). The methods of manufacturing the devices of the different embodiments include machining or molding the components of the valved connector. The spring is manufactured to specification using standard manufacturing techniques. While the device is primarily contemplated for use in human patients, the invention will also have veterinary uses or product development purposes in equine, bovine, canine, feline, and other mammalian species.

The present invention has been described above in terms of certain preferred embodiments so that an understanding of the present invention can be conveyed. However, there are many alternative arrangements not specifically described herein, but with which the present invention is applicable. Although specific features have been provided, the present invention would equally be embodied by other configurations not specifically recited herein. The scope of the present invention should therefore not be limited by the embodiments illustrated, but rather it should be understood that the present invention has wide applicability with respect to valve systems generally. All modifications, variations, or equivalent elements and implementations that are within the scope of the appended claims should therefore be considered within the scope of the invention.

What is claimed as new and desired to be protected by Letters Patent of the United States is:

1. A valved connector for controlling the flow of fluid, comprising:

a connector housing having an inlet and an outlet, the inlet configured to receive a male luer fitting; and a valve assembly having a first position that prevents fluid flow through the connector housing and a second position that permits fluid flow through the connector housing, the valve assembly biased in the first position and movable from the first position to the second position by the male luer fitting, the valve assembly comprising:

a valve element including an upper portion, a slit portion and a lower portion, the upper and lower portions having bores extending through the valve element to the slit portion, the valve element having an outer wall with a reduced outer diameter at the slit portion to create a gap between the valve element and the connector housing, wherein movement of the male luer fitting into the upper portion bore causes the slit portion to open radially by compressing the outer wall against the connector housing; and a support disk having a hole through the center thereof, the valve element positioned on the support disk.

2. The valved connector according to claim 1, wherein said lower portion bore has a frustoconical shape, the smaller diameter portion thereof being adjacent said slit portion and the larger diameter portion thereof being adjacent said support disk.

3. The valved connector according to claim 2, wherein said larger diameter portion is substantially the same as the diameter of said hole in said support disk.

4. The valved connector according to claim 1, wherein said upper portion bore has a frustoconical shape, the smaller diameter portion thereof being adjacent said slit portion and the larger diameter portion thereof being adjacent said inlet.

5. The valved connector according to claim 4, wherein said larger diameter portion is substantially the same as the diameter of an inner surface of said inlet.

6. The valved connector according to claim 1, further comprising a porous mesh or filter.

7. The valved connector according to claim 1, wherein an outside surface of said connector housing surrounding said inlet contains threads for lockingly receiving a threaded luer fitting.

8. The valved connector according to claim 1, wherein an outside surface of said connector housing surrounding said outlet is configured for insertion into the open end of a fluid conduit.

9. The valved connector according to claim 1, wherein said connector housing is adapted for temporary attachment to a catheter.

10. The valved connector according to claim 1, wherein said connector housing is adapted for permanent connection to a catheter.

11. The valved connector according to claim 1, further comprising a catheter, wherein said valved connector is integral with said catheter.

12. The valved connector according to claim 1, wherein said lower portion bore has a frustoconical shape, the smaller diameter portion thereof being adjacent said slit portion and the larger diameter portion thereof being adjacent said support disk, wherein said larger diameter portion is substantially the same as the diameter of said hole in said support disk, wherein said upper portion bore has a frustoconical shape, the smaller diameter portion thereof being adjacent said slit portion and the larger diameter portion thereof being adjacent said inlet, and wherein said larger diameter portion is substantially the same as the diameter of an inner surface of said inlet.

13. The valved connector according to claim 1, wherein the gap spans a longitudinal length of the slit portion.

14. A valved connector for controlling the flow of fluid, comprising:

a connector housing having an inlet at a proximal end and an outlet at a distal end; and a valve assembly positioned in the connector housing, the valve assembly including a valve element and a support disk, a distal end of the valve element positioned proximal of the support disk, the valve element including an upper portion, a lower portion, and a slit portion between the upper portion and the lower portion, the upper portion and the lower portion having respective bores extending through the valve element to the slit portion, the valve element having an outer wall with a reduced outer diameter at the slit portion to create a gap between the valve element and the connector housing, the valve element movable from a first position, preventing fluid flow through the connector housing, to a second position, permitting fluid flow through the connector housing, by a male luer fitting inserted through an opening in the inlet and into contact with the valve element without penetrating the slit portion.

15. The valved connector according to claim 14, wherein the lower portion bore has a frustoconical shape, the smaller diameter portion thereof adjacent the slit portion and the larger diameter portion thereof adjacent the support disk.

16. The valved connector according to claim 15, wherein the larger diameter portion is substantially the same as the diameter of an opening in the support disk.

17. The valved connector according to claim 14, wherein the upper portion bore has a frustoconical shape, the smaller diameter portion thereof adjacent the slit portion and the larger diameter portion thereof adjacent the inlet.

18. The valved connector according to claim 17, wherein the larger diameter portion is substantially the same as the diameter of an inner surface of the inlet.

19. The valved connector according to claim 14, wherein the distal end of the valve element has a distal end surface in contact with a proximal surface of the support disk in the first position and the second position.

20. The valved connector according to claim 14, wherein the upper portion bore and the lower portion bore have frustoconical shapes.

21. A valved connector, comprising:

a connector housing having an inlet at a proximal end and an outlet at a distal end; and a valve assembly positioned in the connector housing, the valve assembly including a valve element positioned proximal of a support disk, a distal surface of the valve element in contact with a proximal surface of the support disk, the valve element having an outer wall with a reduced outer diameter at the slit portion to create a gap between the valve element and the connector housing, the valve element movable from a first closed position to a second open position by a male luer fitting inserted through an opening in the inlet and into contact with an inner surface of a bore in an upper section of the valve element such that the inner surface of the bore is moved radially toward the connector housing, the valve element including a slit through a mid-section, the slit opening when the valve element is moved to the second position to place the upper section bore in fluid communication with a bore in a lower section of the valve element.

* * * * *